US011864865B2

(12) United States Patent
Culver et al.

(10) Patent No.: US 11,864,865 B2
(45) Date of Patent: Jan. 9, 2024

(54) SMALL FORM FACTOR DETECTOR MODULE FOR HIGH DENSITY DIFFUSE OPTICAL TOMOGRAPHY

(71) Applicants: Joseph Culver, St. Louis, MO (US); Edward Richter, St. Louis, MO (US); Adam T. Eggebrecht, St. Louis, MO (US)

(72) Inventors: Joseph Culver, St. Louis, MO (US); Edward Richter, St. Louis, MO (US); Adam T. Eggebrecht, St. Louis, MO (US)

(73) Assignee: Washington University, St. Louis, MO (US)

( * ) Notice: Subject to any disclaimer, the term of this patent is extended or adjusted under 35 U.S.C. 154(b) by 1166 days.

(21) Appl. No.: 16/286,194

(22) Filed: Feb. 26, 2019

(65) Prior Publication Data

US 2019/0261860 A1     Aug. 29, 2019

Related U.S. Application Data

(60) Provisional application No. 62/635,412, filed on Feb. 26, 2018.

(51) Int. Cl.
| | | |
|---|---|---|
| *A61B 5/00* | (2006.01) | |
| *G01B 9/02* | (2022.01) | |
| *G01B 9/02091* | (2022.01) | |
| *A61B 90/00* | (2016.01) | |
| *A61B 90/30* | (2016.01) | |
| *A61B 34/20* | (2016.01) | |

(52) U.S. Cl.
CPC .......... *A61B 5/0066* (2013.01); *A61B 5/0035* (2013.01); *A61B 5/0037* (2013.01);
(Continued)

(58) Field of Classification Search
CPC ... A61B 5/0066; A61B 5/0035; A61B 5/0037; A61B 5/0042; A61B 5/6803;
(Continued)

(56) References Cited

U.S. PATENT DOCUMENTS

| | | |
|---|---|---|
| 6,577,884 B1 | 6/2003 | Boas |
| 7,983,740 B2 | 7/2011 | Culver et al. |

(Continued)

FOREIGN PATENT DOCUMENTS

WO     2016061502 A1     4/2016

OTHER PUBLICATIONS

Eggebrecht, Adam T. et al., "Mapping distributed brain function and networks with diffuse optical tomography," Nature Photonics, 8(6): 448-454 (2014).

*Primary Examiner* — Baisakhi Roy
(74) *Attorney, Agent, or Firm* — Armstrong Teasdale LLP

(57) ABSTRACT

A wearable device for high-density-diffuse optical tomography includes a plurality of source modules that include source housings containing a light source. The device also includes a plurality of detector modules that include detector housings, a photodiodes, transimpedance amplifiers operatively coupled to the photodiodes, and analog to digital converters operatively coupled to the transimpedance amplifier. Each detector housing contains at least one of the photodiode, the analog to digital converter, and the transimpedance amplifier. Each source and detector housing is configurable to contact a subject's scalp and deliver or receive light from the scalp at one position. The wearable device also includes a control circuit operatively coupled to the plurality of source modules and to the plurality of detector modules to operate the source and detector modules in a coordinated manner to acquire a plurality of diffuse optical tomography measurements.

20 Claims, 27 Drawing Sheets
(15 of 27 Drawing Sheet(s) Filed in Color)

(52) U.S. Cl.
CPC .......... *A61B 5/0042* (2013.01); *A61B 5/6803* (2013.01); *A61B 5/684* (2013.01); *G01B 9/02089* (2013.01); *G01B 9/02091* (2013.01); *A61B 2034/2048* (2016.02); *A61B 2090/0807* (2016.02); *A61B 2090/306* (2016.02); *A61B 2090/3614* (2016.02); *A61B 2090/3937* (2016.02); *A61B 2562/0233* (2013.01); *A61B 2576/026* (2013.01)

(58) Field of Classification Search
CPC ............ A61B 5/684; A61B 2090/0807; A61B 2034/2048; A61B 2090/306; A61B 2090/3614; A61B 2090/3937; A61B 2562/0233; A61B 2576/026; A61B 5/0053; A61B 5/7225; A61B 5/0091; A61B 5/0073; G01B 9/02089; G01B 9/02091
See application file for complete search history.

(56) References Cited

U.S. PATENT DOCUMENTS

| | | | |
|---|---|---|---|
| 9,037,216 B2* | 5/2015 | Hielscher | A61B 5/0053 382/128 |
| 2007/0106172 A1* | 5/2007 | Abreu | A61P 7/02 600/549 |
| 2007/0272260 A1* | 11/2007 | Nikitin | A61N 1/0529 128/899 |
| 2009/0105605 A1* | 4/2009 | Abreu | A61B 5/4076 600/549 |
| 2010/0016732 A1 | 1/2010 | Wells et al. | |
| 2010/0219820 A1* | 9/2010 | Skidmore | G01R 33/0354 324/247 |
| 2010/0292569 A1* | 11/2010 | Hielscher | A61B 5/0091 600/425 |
| 2011/0309236 A1* | 12/2011 | Tian | H01L 27/14638 257/E31.097 |
| 2014/0275891 A1* | 9/2014 | Muehlemann | A61B 5/0042 600/328 |
| 2014/0276013 A1* | 9/2014 | Muehlemann | A61B 5/0073 600/425 |
| 2014/0276014 A1* | 9/2014 | Khanicheh | A61B 5/0073 600/425 |
| 2015/0094914 A1* | 4/2015 | Abreu | B60H 1/00742 701/1 |
| 2015/0223697 A1* | 8/2015 | Hielscher | A61B 5/0053 600/425 |
| 2016/0143541 A1* | 5/2016 | He | A61B 5/374 600/407 |
| 2017/0224246 A1* | 8/2017 | Jiang | A61B 5/6803 |

* cited by examiner

FIG. 11A MRI-based atlas with segmented head structure

FIG. 11B Subject head surface

PRIOR ART

SMALL FORM FACTOR DETECTOR MODULE FOR HIGH DENSITY DIFFUSE OPTICAL TOMOGRAPHY

CROSS-REFERENCE TO RELATED APPLICATIONS

This application claims the benefit of priority to U.S. Provisional Patent Application No. 62/635,412, filed Feb. 26, 2018, the entire disclosure of which is incorporated herein by reference.

STATEMENT REGARDING FEDERALLY SPONSORED RESEARCH & DEVELOPMENT

This invention was made with government support under grant R01NS090874, awarded by the National Institutes of Health. The government has certain rights in the invention.

BACKGROUND

Non-invasive functional neuroimaging has enabled mapping of brain function and revolutionized cognitive neuroscience. The role of functional neuroimaging is expanding as both a diagnostic and prognostic tool in a variety of clinical populations, including younger age groups. The broadening and expanding application of functional neuroimaging in the study of both healthy and disease states necessitates new and more flexible systems and methods.

Diffuse optical imaging ("DOI") is an imaging methodology that can be utilized in mapping the functional activity in the human brain. With unique capabilities that include functional neuroimaging method, DOI complements and expands upon the other more established modalities such as Positron Emission Tomography ("PET") and Magnetic Resonance Imaging ("MRI"). While tremendously useful, the scanning environments of MRI and PET brain instruments generally require a fixed head placement in an enclosed tube, with significant scanner noise such as that found with MIII or the use of radioactive isotopes such as that found with PET.

The logistics of traditional functional brain scanners (e.g., fMRI), which weigh several tons and require fixing the head position, are ill-suited to a portion of the clinical population, in particular subjects in MRI scanners who cannot lie sufficiently still to capture usable imaging data. Many high-resolution medical imaging methods such as MRI used for neuroimaging, require highly stationary subjects, and usage may be precluded for young children under 5 years old.

In marked contrast to the more expensive scanner based technology (e.g. MM and PET), DOI employs a less extensive technology platform and a wearable imaging cap. The DOI cap is well suited for several situations that are not amenable to fixed scanner environments, including the ability to obtain images of moving subjects who might otherwise require sedation, unmovable subjects, non-communicative subjects, patients in intensive care, subjects with metal implants, as well as studies of human development in children that would benefit from enriched ecological environments for a wider range of behavioral paradigms. The application that has particularly high potential is the use of DOI for critical care monitoring of infants and neonates.

Diffuse Optical Imaging ("DOI") builds images out of a number of discrete source and detector pair ("optode-pair") near-infrared spectroscopic samplings that are made non-invasively. When there is a single point measurement that is utilized without imaging, utilizing one or just a few optode pairs, the technique is referred to as near-infrared spectroscopy ("NIRS").

Previous diffuse optical neuroimaging systems have utilized sparse imaging arrays such as that disclosed in FIG. 19, which are generally indicated by numeral 10. In this scenario, sources are indicated by numeral 12 and detectors are indicated by numeral 14. The lines shown between the sources and detectors are the available source-detector measurement pairs, which are configured only as nearest neighbor optode pairs.

Referring now to FIG. 20, illustrating a sparse optode grid is generally indicated by numeral 20 in which the sources are indicated by numeral 24 and the receptors are indicated by numeral 26. The recreated simulated image is generally indicated by numeral 30 where the simulated reconstructed image for analysis is indicated by numeral 32.

The most extensively utilized NIRS brain imaging machine is restricted to first (1st) nearest neighbor measurements only and topography, e.g., HITACHI® ETG-100 OT and ETG-400 OT, although high frame rates can be achieved. The type of system and the use of the nearest neighbor optode pairs have limited lateral resolution and no depth-sectioning capabilities. Simulations indicate that increasing the density of the optode arrays can improve resolution, localization and cerebral signal discrimination. However high density optode grids place stringent requirements upon the dynamic range, crosstalk, channel count and bandwidth performance specifications of the instrumentation, and these challenges are unmet by previous systems.

FIG. 21 illustrates a rudimentary schematic of a prior art source detector multiplexing system, which is generally indicated by numeral 100. Typically an analog input and output device indicated by 110 is connected to analog sources 112 which are then multiplexed 114, typically time encoding of the signal, into different source optode locations provided through a plurality of connectors 115 to the measurement subject, e.g., human user, 116. After interacting with the measurement subject, e.g., human user, 116, the detector multiplexing system 118 decodes the time coding via light conductors 117, e.g., fiber optic cables. The light is then received by the detectors 120 and preprocessed in the gain stages 122 and then stored. The signal is converted to a digital signal through the analog digital converter 124. All of the illustrated stages 110, 112, 114, 118, 120, 122 and 124 take into account any change in encoding strategy or optode grid design.

A typical detector system is indicated by numeral 130 in FIG. 22. Light 131 is received in a series of channels 132 through a plurality of detectors 133, e.g., silicon photo diodes ("SiPD") that are connected to a programmable gain stage 134. After the first gain stage 134, there are a plurality of lock-in stages generally indicated by numeral 140. A lock-in frequency is a type of amplifier that can extract a signal with a known carrier wave from a noisy environment. There are represented a first lock-in frequency amplifier 142 and a second lock-in-frequency amplifier 144 for extracting at least two separate frequencies. The signals, after passing through programmable gain arrays 145, are then sent to sampling and hold stages 146. These digital signals are then provided to a processor 148. Therefore, there are significant issues when it comes to multiplexing as well as other significant issues involving both dynamic range and crosstalk.

SUMMARY

In one aspect, a detector module for a high-density diffuse optical tomography instrument is disclosed. The detector module includes a photodiode, a transimpedance amplifier operatively coupled to the photodiode, and an analog to digital converter operatively coupled to the transimpedance amplifier. The housing contains at least one of the photodiode, the transimpedance amplifier, and the analog to digital converter. The detector module is configured to receive light from a scalp of a subject at a detector position.

In another aspect, a wearable device for high-density-diffuse optical tomography is disclosed. The wearable device includes a plurality of source modules. Each source module includes a source housing containing a light source. Each source housing is configurable to contact a scalp of a subject and to deliver light into the scalp at one source position of a plurality of source positions. The wearable device also includes a plurality of detector modules. Each detector module includes a detector housing, a photodiode, a transimpedance amplifier operatively coupled to the photodiode, and an analog to digital converter operatively coupled to the transimpedance amplifier. Each detector housing contains at least one of the photodiode, the analog to digital converter, and the transimpedance amplifier. Each detector housing is configurable to receive light from the scalp at one detector position of a plurality of detector positions. The wearable device also includes a control circuit operatively coupled to the plurality of source modules and to the plurality of detector modules. The control circuit is configured to operate the plurality of source modules and the plurality of detector modules in a coordinated manner to acquire a plurality of diffuse optical tomography measurements.

In an additional aspect, a method for obtaining a series of brain activity maps of a subject using a wearable high-density diffuse optical tomography (WHD-DOT) device is disclosed. The method includes fitting the WHD-DOT device to a scalp of the subject. The WHD-DOT device includes a flexible cap, a plurality of source modules and detector modules coupled to the flexible cap in an array pattern, and a control circuit comprising at least one control module selected from the group consisting of a microcontroller, a central processing unit, and a field programmable gate array. The at least one control module is operatively coupled to the plurality of source modules and detector modules. The at least one control module is configured to operate the plurality of source modules and detector modules according to at least one encoding scheme. Each source module and detector module includes a housing with a maximum width ranging from about 1 mm to about 6 mm and a length ranging from about 10 mm to about 30 mm. The method also includes operating, under control of the at least one control module, the plurality of source modules and detector modules to obtain a plurality of diffuse optical tomography measurements. Each diffuse optical tomography measurement is associated with a source-detector channel of the WHD-DOT device.

DESCRIPTION OF THE DRAWINGS

The patent or application file contains at least one drawing executed in color. Copies of this patent or patent application publication with color drawing(s) will be provided by the Office upon request and payment of the necessary fee.

FIG. 11A is an image showing a reference anatomy in the form of an MM-based atlas with segmented internal head structures;

FIG. 11B is an image showing a subject head model obtained by transformation of the reference anatomy;

Figure 1:
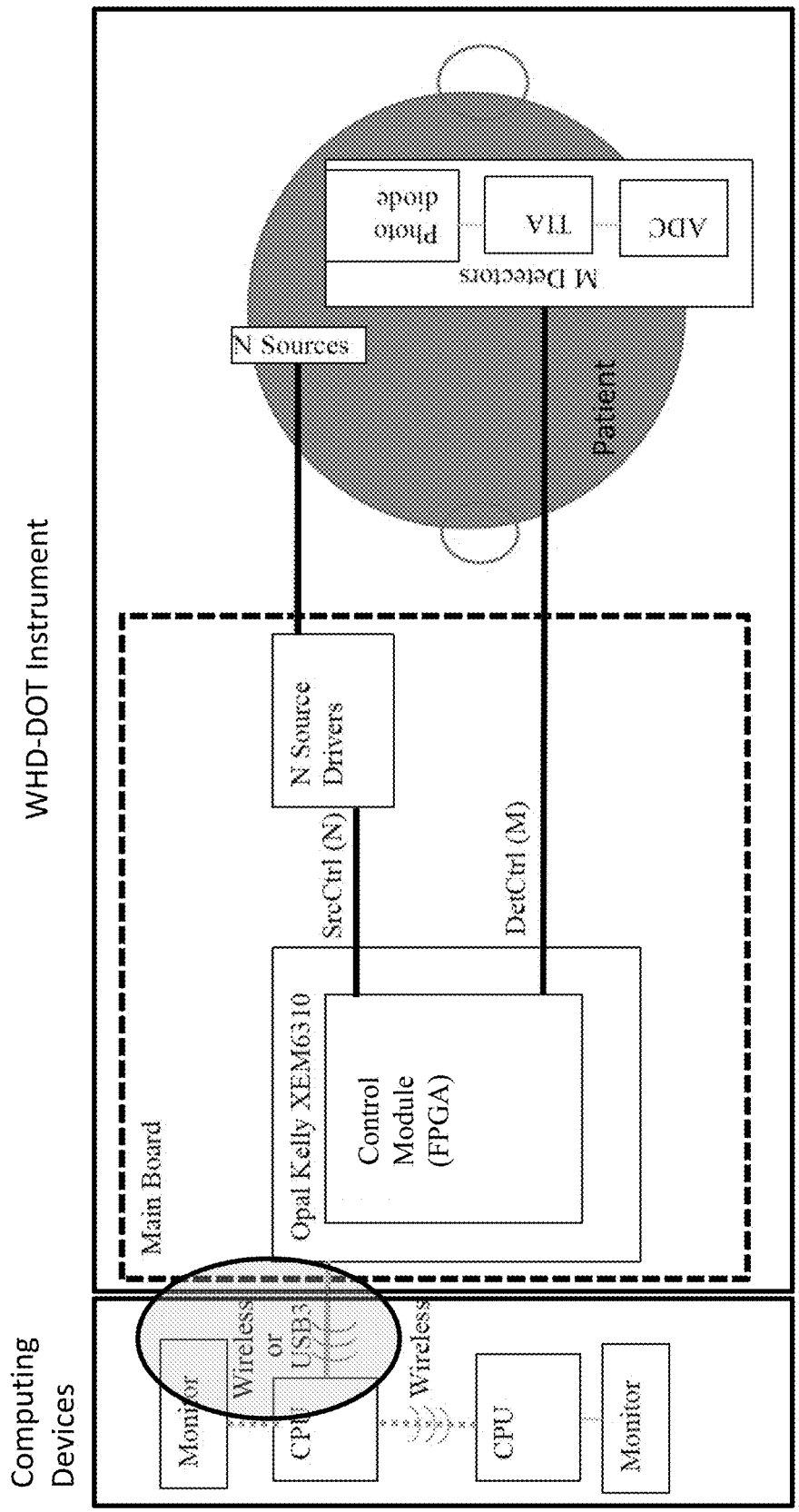
FIG. 1 is a schematic diagram of a high density-diffuse optical tomography (HD-DOT) system in accordance with one aspect of the disclosure.

There are shown in the drawings arrangements which are presently discussed, it being understood, however, that the present embodiments are not limited to the precise arrangements and are instrumentalities shown. While multiple embodiments are disclosed, still other embodiments of the present disclosure will become apparent to those skilled in the art from the following detailed description, which shows and describes illustrative aspects of the disclosure. As will be realized, the invention is capable of modifications in various aspects, all without departing from the spirit and scope of the present disclosure. Accordingly, the drawings and detailed description are to be regarded as illustrative in nature and not restrictive.

DETAILED DESCRIPTION

In various aspects, a wearable high-performance high-density diffuse optical tomography (WHD-DOT) device provided with a plurality of features to enable mapping of brain function of a subject in naturalistic settings is described herein. The disclosed WHD-DOT device includes a miniaturized version of a high-density diffuse optical tomography (HD-DOT) system modified to position at least a portion of the sensitive detector electronics directly on the subject's head, resulting in reduced noise, device weight, and power requirements, while matching the performance of existing DOT devices, such as fiber-based high-density Diffuse Optical Tomography (HD-DOT) devices used in existing HD-DOT systems.

Figure 23:
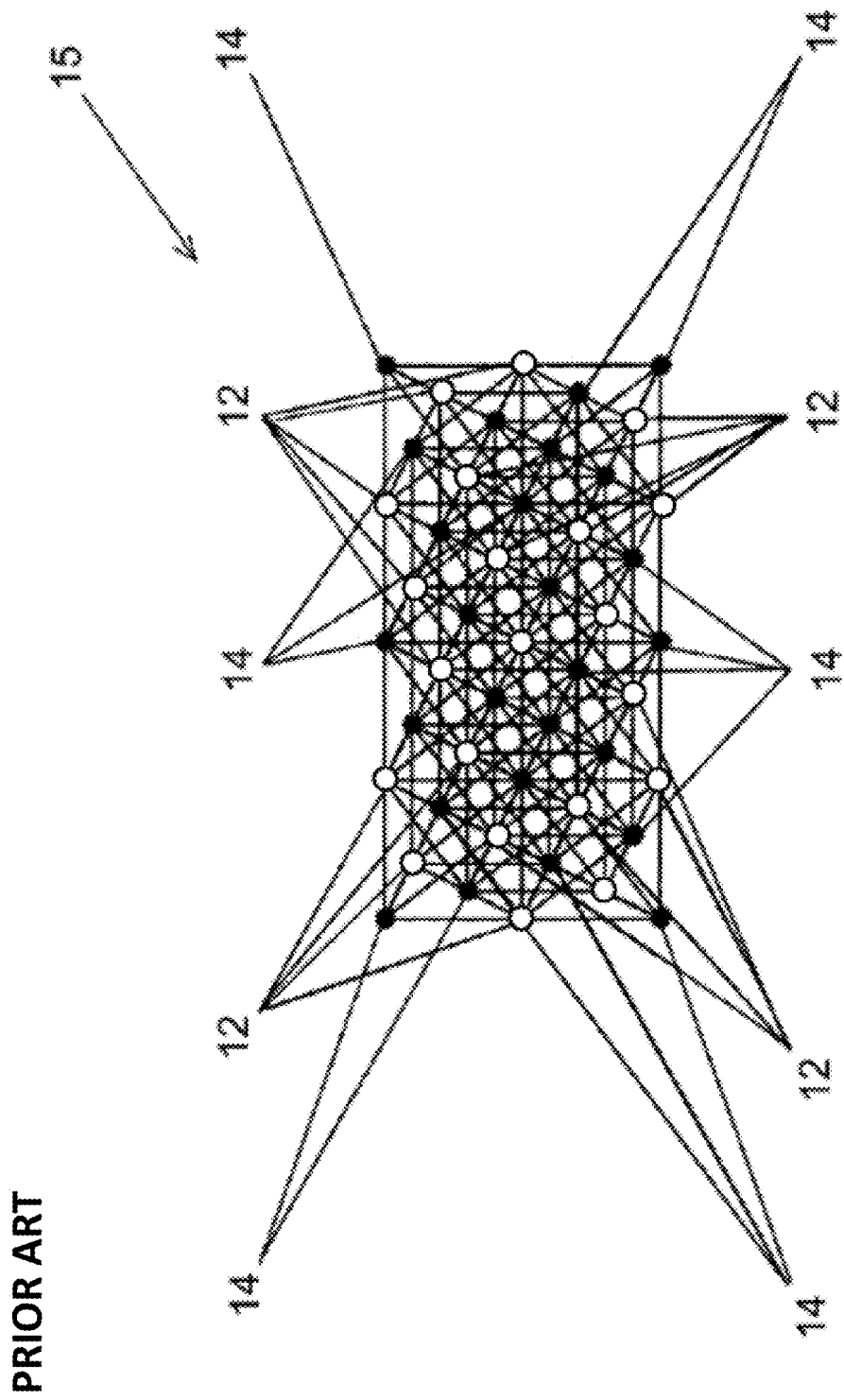
FIG. 23 is a representation of diffuse optical imaging utilizing high density optode pairs.

HD-DOT systems incorporate dense grid imaging arrays, such as shown in FIG. 23 and generally indicated by numeral 15. In this dense grid imaging array, measurements are taken over multiple source detector distances with the sources identified by numeral 12 and detectors indicated by numeral 14. This high density array significantly improves lateral resolution and allows for volumetric localization of the functional signals to enable depth profiling of the subject. The high density array enables signals to be received by detectors from sources at a range of separation distances, also referred to herein as nearest-neighbor distances. The signals received from immediately adjacent sources (i.e. first nearest neighbor source-detector pairs) capture information characteristic of the properties of tissues near the surface of the subject, including, but not limited to scalp and skull bone tissues. Signals received from sources at higher separation distances (i.e. $2^{nd}$ nearest neighbor source-detector pairs, $3^{rd}$ nearest neighbor source-detector pairs, $4^{th}$ nearest neighbor source-detector pairs, and so on) capture information characteristic of the properties of deeper tissues including, but not limited to, brain tissue. Consequently, the signals received from more widely separated source-detector pairs contain more information regarding brain function to enable brain mapping.

In various aspects, the first nearest-neighbor distance ranges from about 0.5 cm to about 1.3 cm, the second nearest neighbor distance ranges from about 1.0 to about 3.0 cm, the third and fourth nearest neighbor distances range from about 1.0 and about 5.0 cm. Without being limited to any particular theory, the nearest-neighbor distances may be selected to enable detection of light from a source at the detector of a source-detector pair, reduce cross-talk form other source-detector channels, enable the acquisition of diffuse optical tomography data at a resolution suitable for functional brain mapping, the dimensions of the source and detector modules, and any other relevant factor without limitation.

High density diffuse optical arrays include a plurality of source-detector pair measurements with overlapping samplings that also permit diffuse optical tomography (DOT) reconstructions. Consequently, the quality of high density diffuse optical tomography depend on designs that enable very high dynamic range and low crosstalk to simultaneously measure multiple signals at multiple distances with a significant number of measurements. Dynamic range is defined as the ratio of the maximum light power divided by the minimum detectable light power (or noise equivalent light level power). Furthermore, neuroimaging involves imaging a variety of time variant physiology, including heart pulse (1 Hz), breathing (0.1 to 1 Hz), and neuronally activated hemodynamic (0.001 to 0.3 Hz) and fast scattering (10 Hz to 1 KHz) responses. Therefore, high speed frame rates of greater than 1 Hz enable significant advantages as frame rates progress in speed up to 1 KHz. The dynamic range and crosstalk performance are typically maintained at the operating frame rates described above.

Low frame speed and significant crosstalk may significantly degrade the quality of high density diffuse optical tomography. "Crosstalk" is defined as the leakage (or "bleeding") of signal from one channel into another. In various aspects, HD-DOT systems make use of source channels, detector channels and source-detector pair channels. The channels most significantly impacted by crosstalk in HD-DOT systems are typically source-detector pair channels. Crosstalk between source channels or between detector channels creates crosstalk between source-detector channels.

Figure 19:
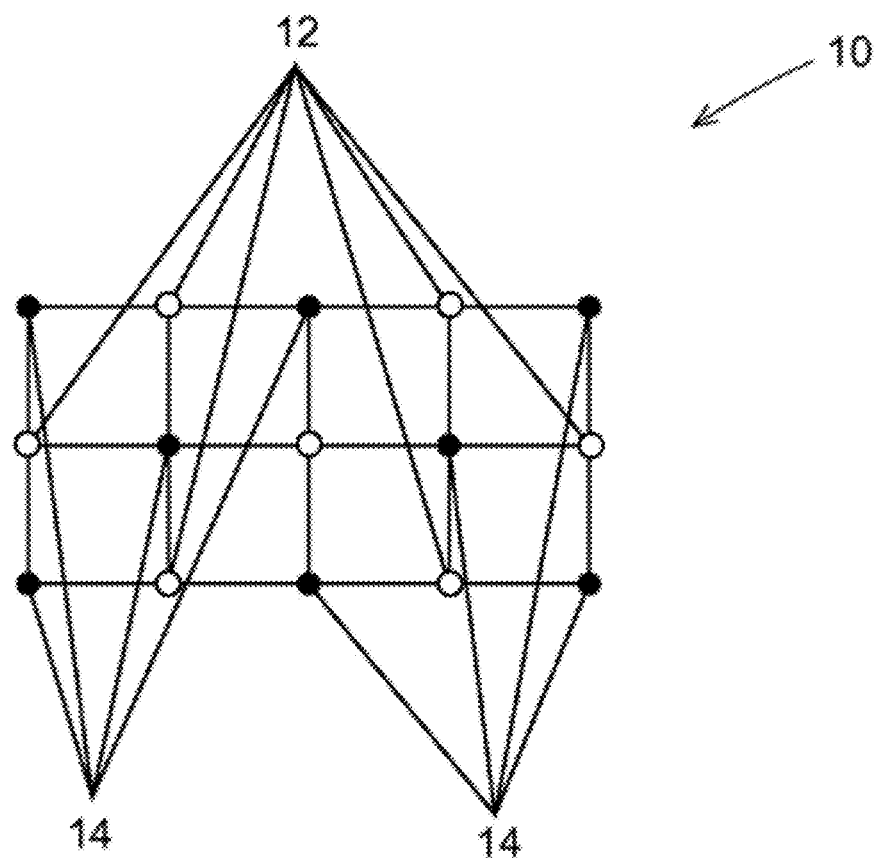
FIG. 19 is a representation of diffuse optical imaging utilizing sparse optode pairs.
Figure 20:
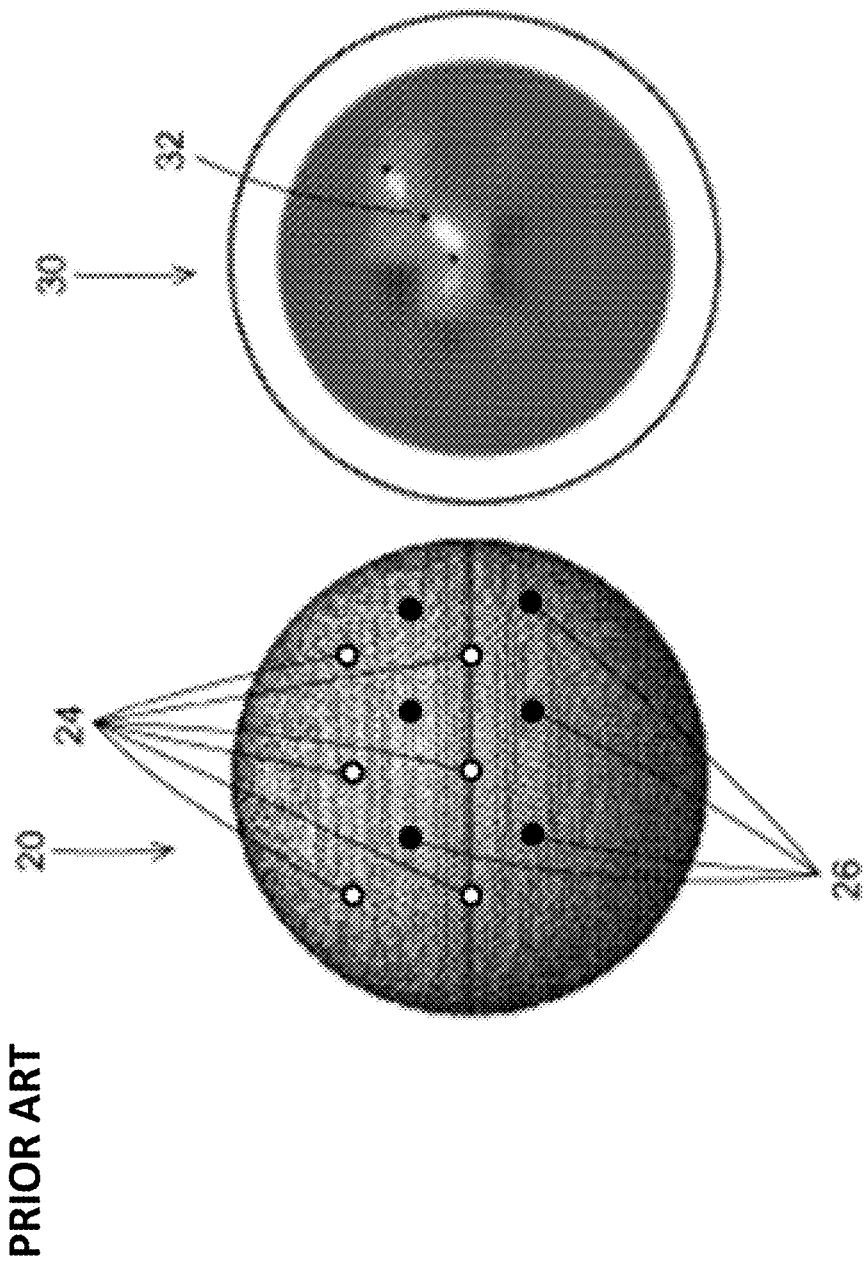
FIG. 20 is a representation of image quality, with image reconstruction, for diffuse optical imaging utilizing sparse optode pairs.
Figure 21:
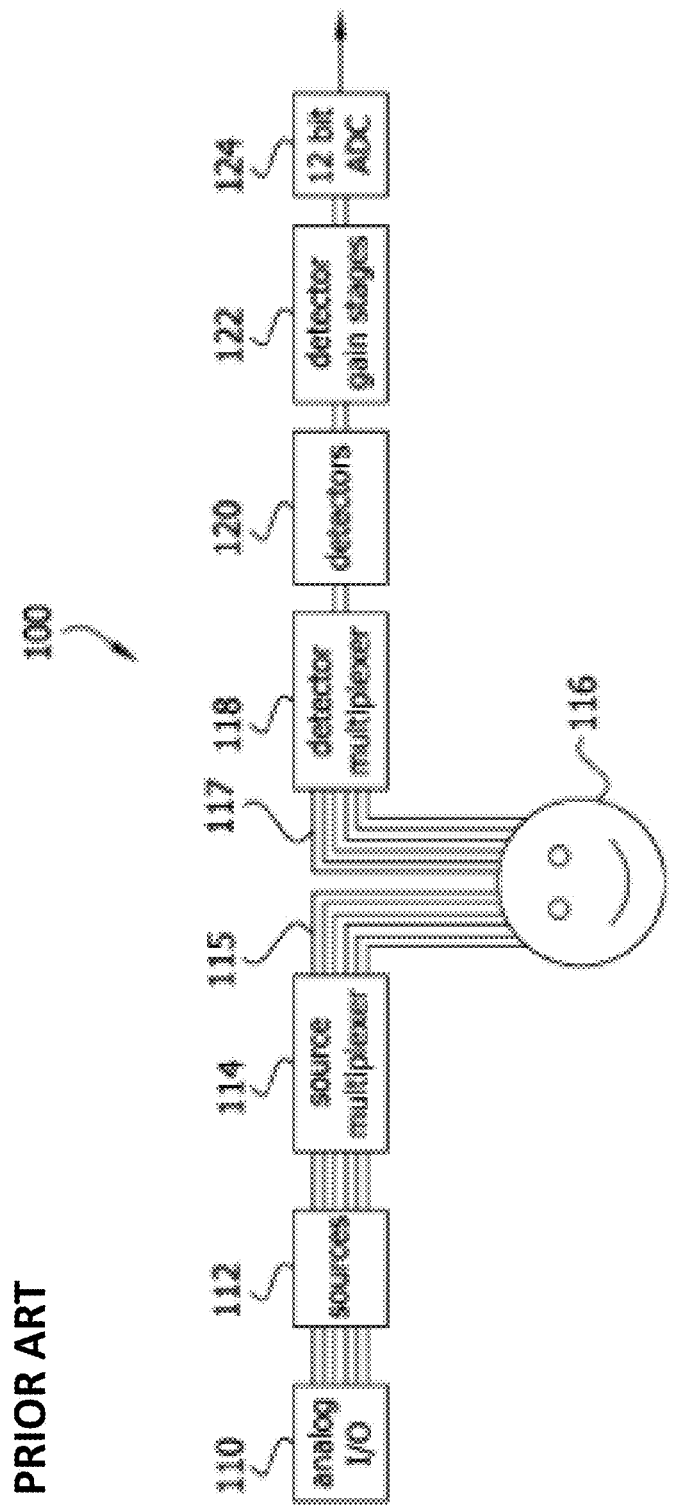
FIG. 21 is a flowchart of source and detector multiplexing and gain stages.
Figure 22:
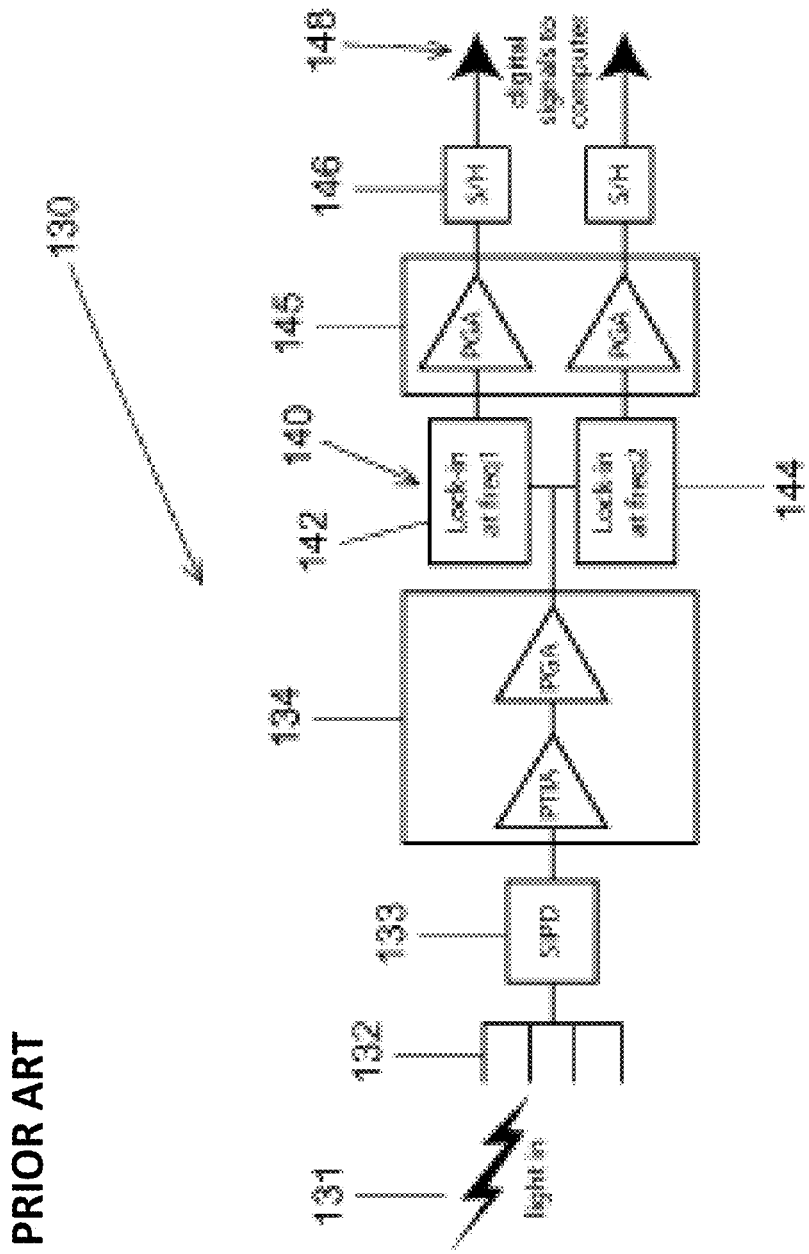
FIG. 22 is a flowchart of detection system with a series of programmable gain stages.

A number of challenges involving both dynamic range and crosstalk exist within HD-DOT systems. For example, as shown in FIG. 23, the high density optode grid indicated by numeral 15 presents significant challenges as compared to the low density optode grid indicated by numeral 10 in FIG. 19. The detectors 14 within the sparse grid 10 of FIG. 19 need only a dynamic range sufficient to accommodate the range of intensities in the nearest neighbor signals, where dynamic range is the signal to dark noise level. In the high density grid 15 of FIG. 23, the dynamic range must be large enough to measure the high signals from the nearest neighbor pairs as well as the significantly smaller signal variations from the third or fourth nearest neighbor pairs.

Crosstalk occurs when the signal from one optode pair measurement registers on another measurement channel. With a broader range of signal levels being measured, sensitivity to crosstalk is enhanced in the dense grids 15 of FIG. 23. Crosstalk can occur at the source level when the output signal from one source is also included in the output provided by other sources. At the detector level, a signal from one detector may bleed over to other detector channels and a similar situation can occur in the analog-to-digital circuitry. The presence of crosstalk is a significant factor that may corrupt the signal quality in lower level channels and is typically minimized to facilitate tomography.

Figure 24:
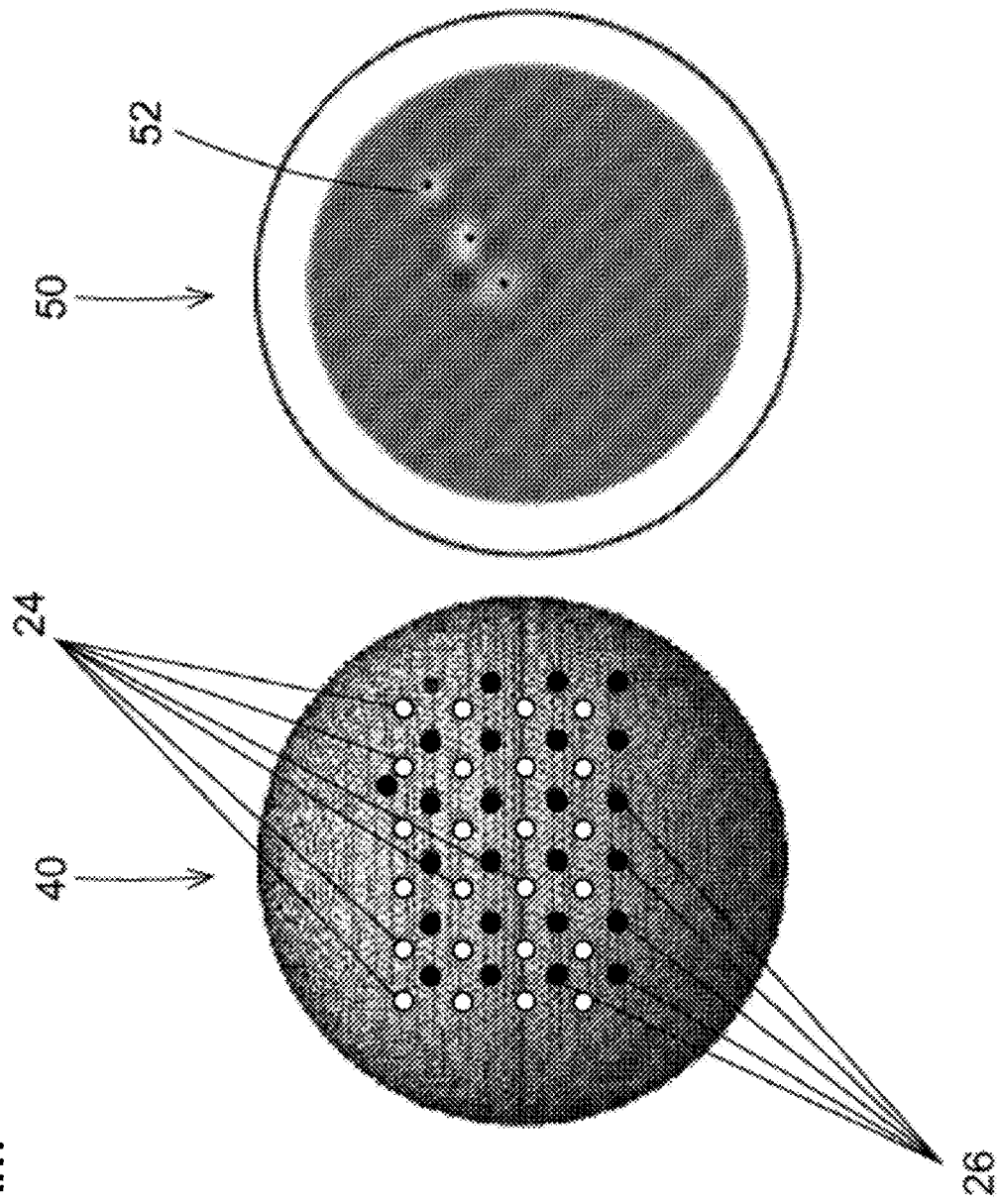
FIG. 24 is a representation of image quality, with image reconstruction, for diffuse optical imaging utilizing dense optode pairs.

FIG. 24 illustrates a dense source-detector grid generally indicated by numeral 40 that includes sources 24 and detectors 26. The simulated image is generally indicated by numeral 50 and the stimulated image reconstruction indicated by numeral 52. A number of approaches may be implemented to increase the speed of the system as well as decrease crosstalk. In one aspect, these approaches include some type of encoding strategy.

In various aspects, encoding strategies include time encoding, frequency encoding and spatial encoding. Time encoding decreases signal crosstalk by switching only particular sources at a particular time step. Frequency encoding assigns specific modulation frequencies to different signals, which enables multiple sources to be on simultaneously and consequently increases the measurement rate of the system. Frequency specific detection schemes separate out the required signals by limiting inter-channel separation by the level of background shot noise. Spatial encoding also increases the measurement rate by allowing optode pairs in different regions of the pad to be activated simultaneously. Spatial separation provides another approach to reducing crosstalk for distant optodes, but is less effective at reducing crosstalk for optodes that are close together. A combination of all three encoding strategies may optimize of image quality for a variety of head sizes and imaging tasks, but necessitates a high level of system flexibility to achieve.

In various aspects, depth sectioning is enabled using the high density optode grid measurements described above. The greater source detector separations allow sampling deeper into the tissue; therefore, simultaneous measurements at multiple separation distances can provide the necessary information to separate depth dependent signals. Non-limiting examples of existing multi-distance measurement systems for brain imaging include the DYNOT™ system by NIRX™ which has 32 sources and 32 detectors and the ISS Imagent system with eight (8) detectors and two (2) continuous wave ("CW") systems developed by Massachusetts General Hospital known as "CW4" which has nine (9) sources and sixteen (16) detectors and "CW5" which has 16 sources and 32 detectors.

One limitation of the existing multi-distance measurement systems described above is associated with the use of time-shared, multiplexed analog-to-digital converters (ADCs). Typically, multiplexed analog-to-digital converter acquisition cards have inter-channel crosstalk values of greater than −75 dB. In some multi-distance measurement systems, 16-bit analog-to-digital converters have been used which have an inherent dynamic range of less than $10^5$ in many systems. Analog gain adjustments are made to match the signal range (dark noise to maximum signal) for a given measurement to the range of analog-to-digital converter electronics. These dynamic gain adjustments between neighboring channels can increase the effective crosstalk between detector channels and the effective dynamic range of the device. However, these dynamic gain adjustments at high speeds become very complex and are prone to new sources of channel crosstalk. The time-shared adjustable detector circuitry limits the number of measurements that can be taken simultaneously and affects the overall speed of the system.

Another limitation of the existing multi-distance measurement systems described above that include high channel counts is the use of source encoding and decoding strategies that are determined and implemented by hardware. Examples include fully timed multiplexed light sources in which a single light source is shared between multiple source locations or fully frequency encoded systems or a fixed mixture of frequency and time encoding. These hardware approaches dramatically decrease the flexibility with regard to encoding strategy resulting in increased crosstalk, decreased signal noise ratios, slower imaging times and degraded image quality.

Table 1 below compares the performance capabilities of the WHD-DOT device, systems, and methods to other existing functional neuroimaging systems and methods, including fiber-based HD-DOT), wireless functional near-infrared spectroscopy (WIFI-fNIRS), functional magnetic resonance imaging (fMRI), positron emission tomography (PET), electroencephalography (EEG), electrocorticography (EcoG), and magnetoencephalography (MEG). Of the functional neuroimaging devices and methods compared in Table 1, only the WHD-DOT, WIFI-fNIRS, and EEG devices are wearable to the extent that a subject may move relatively freely during neuroimaging. Of the wearable neuroimaging devices, only WHD-DOT device enables neuroimaging at spatial resolution that approaches the corresponding spatial resolution of much larger and immobile devices, such as fMRI or PET scanners. The higher spatial resolution of the WHD-DOT device potentially enables the ability to map brain function in clinical populations previously precluded from such functional neuroimaging experiences due to subject movements associated with the subject's age (i.e. younger than about six or older than about fifty years old), the subject's mental status, clinical status, and/or the subject's neuromuscular condition including, but not limited to, cerebral palsy or Parkinson's.

TABLE 1

Comparison of Functional Neuroimaging Techniques

| | Functional Neuroimaging Method | | | | | | | |
|---|---|---|---|---|---|---|---|---|
| Type | Hemoglobin and Blood Flow | | | | | Electrical | | |
| Performance Parameter | WHD-DOT | HD-DOT | WIFI-fNIRS | fMRI | PET | EEG | EcoG | MEG |
| Wearable | Yes | No | Yes | No | No | Yes | Med | No |
| Non-Ionizing | Yes | Yes | Yes | Yes | No | Yes | Yes | Yes |
| Non-Invasive | Yes | Yes | Yes | Yes | Yes | Yes | No | Yes |
| Spatial Resolution | Med+ | Med+ | Low | High | Med | Low | High | Med+ |
| Field of View | Med | Med | Low | High | High | Low | Med | Med |
| Temporal Resolution | Med | Med | Med | Med | Low | High | High | High |

Figure 4:
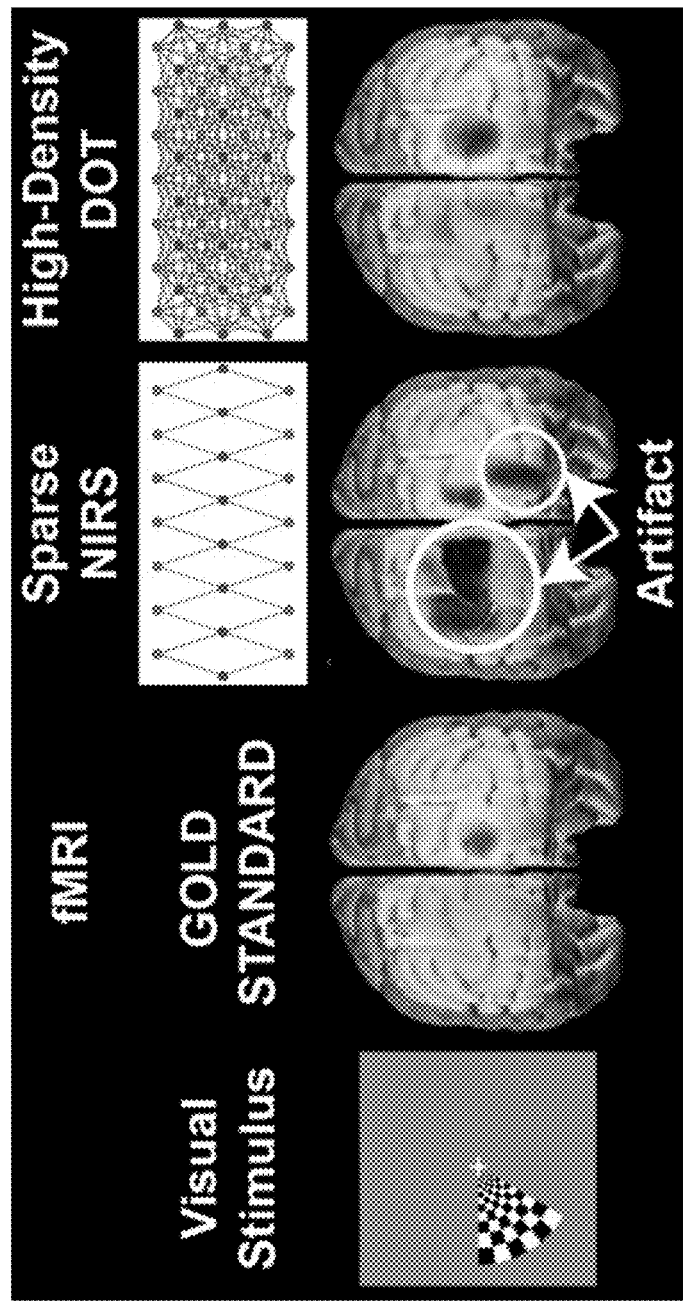
FIG. 4 is an image comparing the brain images obtained using Mill, NIRS, and HD-DOT methods.

In various aspects, the incorporation of high-density DOT imaging array technology into the WHD-DOT device enables a higher spatial sampling, and a greater array of source-detector separations relative to existing optically-based neuroimaging technologies, such as fNIRS, as illustrated in FIG. 4. Existing fNIRS systems that make use of wearable fNIRS devices typically include relatively low numbers of source-detector channels, ranging from about 25 channels to about 40 channels, and may further include source/detector module sizes of larger than 25 mm×25 mm. Existing fiber-based HD-DOT scanners (see FIG. 5A) include about 100-fold more source-detector channels compared to existing wearable fNIRS devices. Consequently, fiber-based high-density diffuse optical tomography (HD-DOT) technology enables neuroimaging at spatial resolutions approaching the correspondingly high spatial resolutions of fMRI neuroimaging, as illustrated in FIG. 4. For image quality, simulations suggest that even the largest fiber-based HD-DOT scanners, which may include as many as 1800 source-detector channels, underperform a theoretically optimal space bandwidth product by 10-fold to 20-fold.

Figures 5A, 5B, 5C:
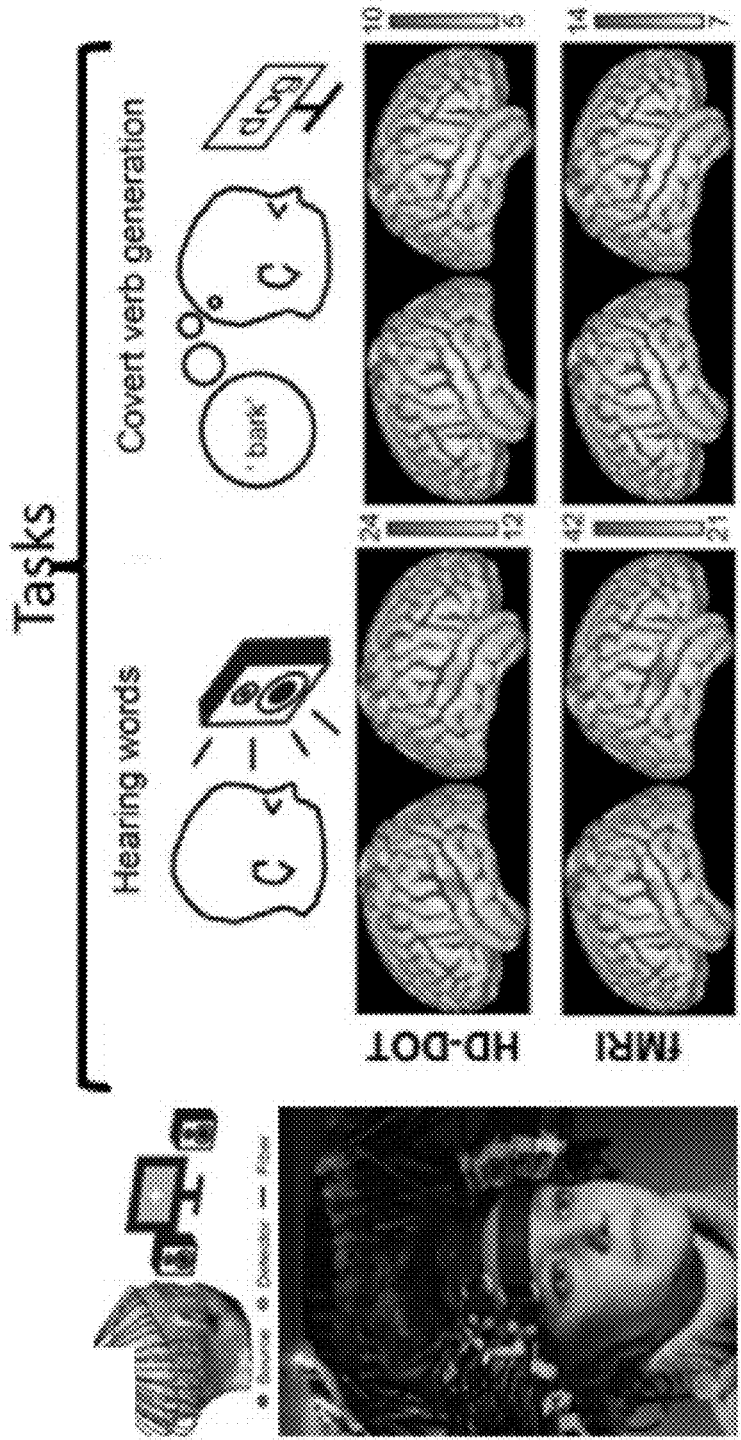
FIG. 5A is a schematic illustration of an existing fiber-based HD-DOT system and wearable sensor array for mapping distributed brain functions and networks.
FIG. 5B contains images of functional maps obtained from a subject while hearing words using the HD-DOT system illustrated in FIG. 5A (top map) and obtained using Mill (bottom map)
FIG. 5C contains images of functional maps obtained from a subject performing a covert verb generation task using the HD-DOT system illustrated in FIG. 5A (top map) and obtained using fMRI (bottom map)
Figures 5D, 5E, 5F:
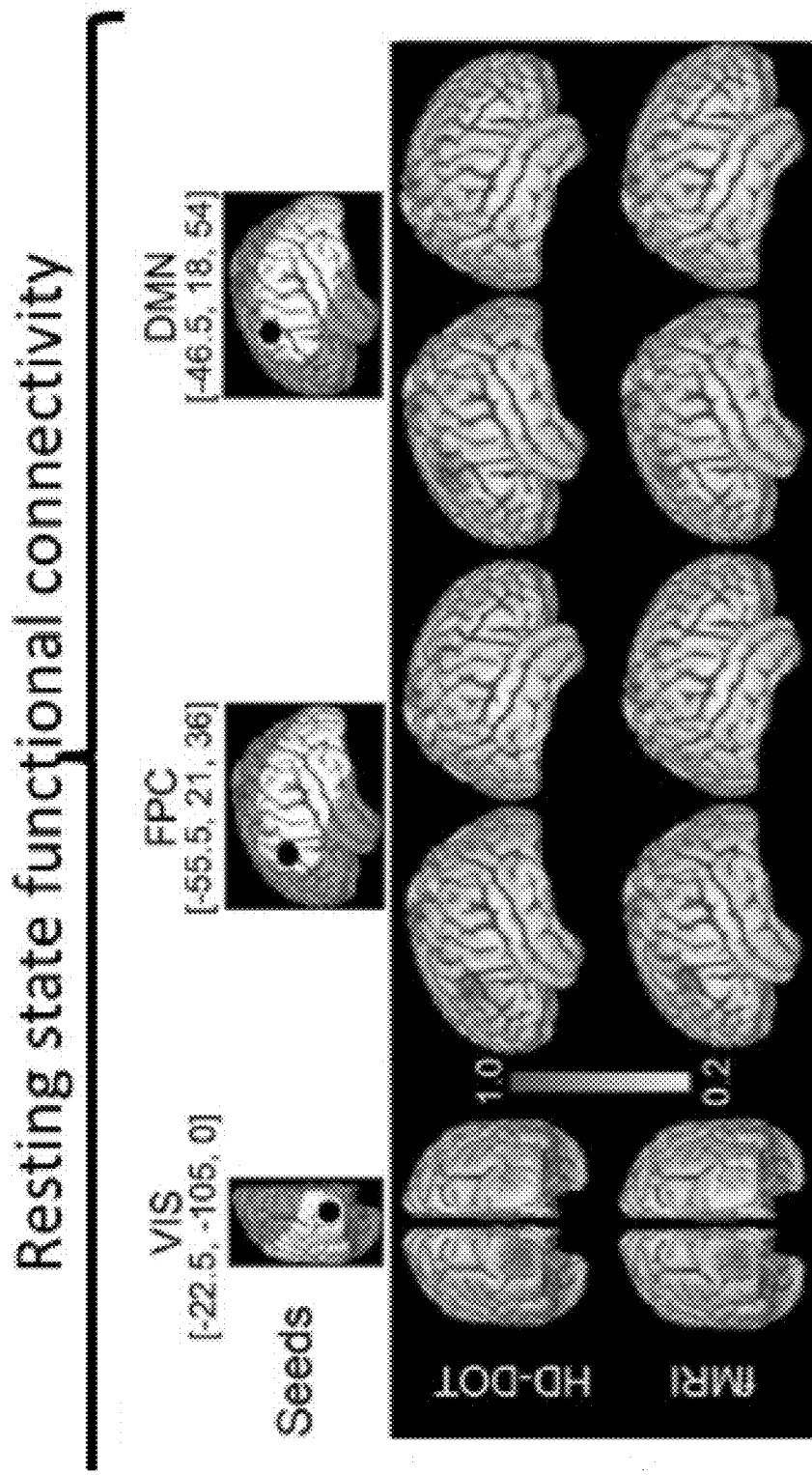
FIG. 5D contains images of resting state functional connectivity maps for the visual (VIS) resting state network (RSN) using the HD-DOT system illustrated in FIG. 5A (top map) and obtained using fMRI (bottom map)
FIG. 5E contains images of resting state functional connectivity maps for the Frontal Parietal Cortex (FPC) resting state network (RSN) using the HD-DOT system illustrated in FIG. 5A (top map) and obtained using fMRI (bottom map)
FIG. 5F contains images of resting state functional connectivity maps for the Default Mode (DMN) resting state network (RSN) using the HD-DOT system illustrated in FIG. 5A (top map) and obtained using fMRI (bottom map)

Referring again to FIG. 4, as compared to fMRI, HD-DOT imaging can achieve localization errors of less than about 5 mm, and point spread functions of less than about 15 mm full width at half maximum (FWHM), an image quality that is sufficient to localize functions to gyri (see FIG. 5B and FIG. 5C). While initially confined to simpler sensory networks, such as visual and motor (see FIG. 5D), recent results have demonstrated the feasibility of mapping distributed cognitive networks, including the frontal parietal (see FIG. 5E) and default mode networks (see FIG. 5F) using HD-DOT technology.

Figure 6:
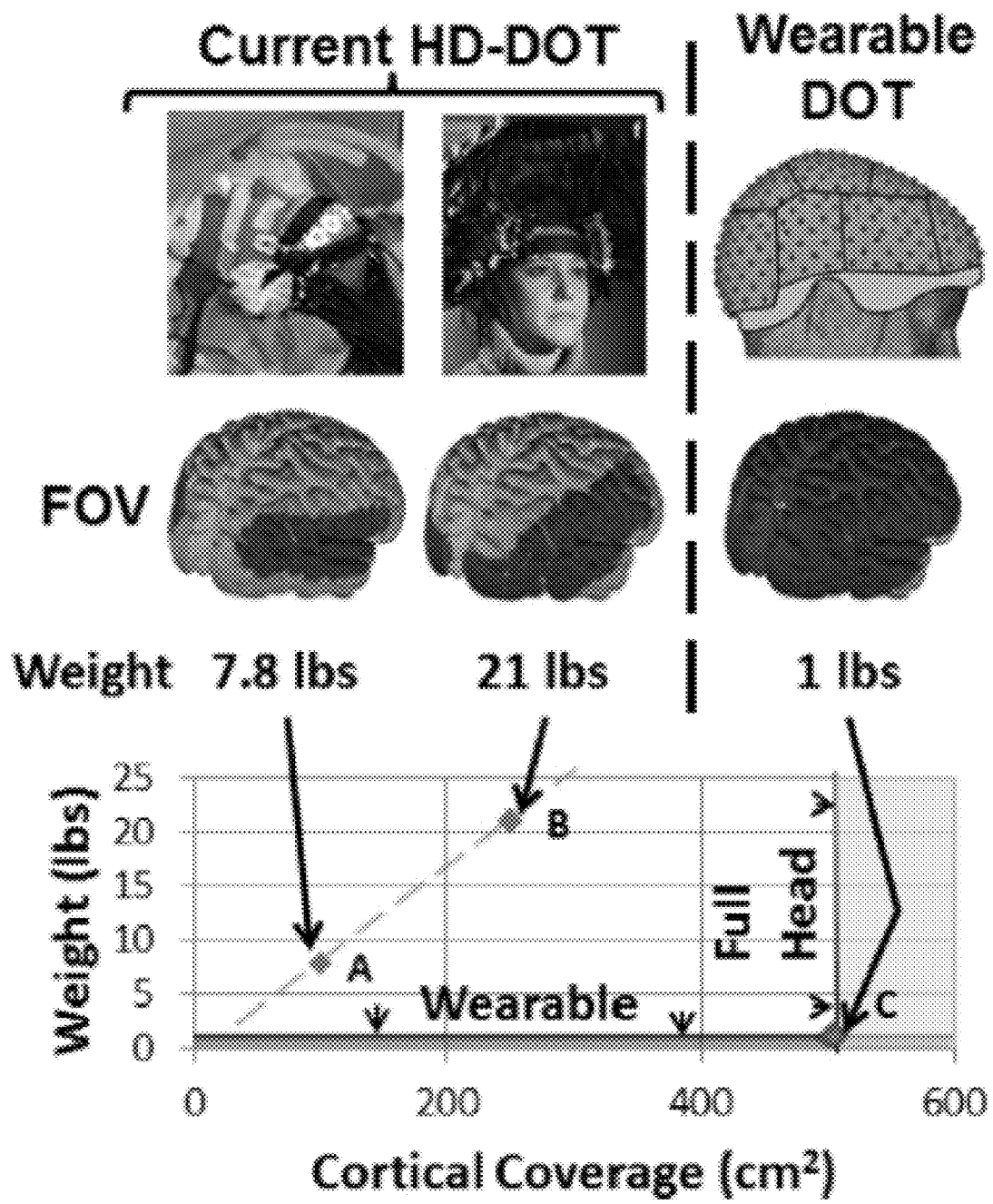
FIG. 6 is a graph of device weight as a function of cortical coverage for a variety of existing fiber-based HD-DOT and a wearable WHD-DOT instruments in accordance with one aspect of the disclosure.

In various aspects, the incorporation of miniaturized source modules and detection modules into the design of the WHD-DOT device obviates the need for bulky optical fibers, enabling higher spatial sampling density of the sources and detectors, larger areas of cortical coverage, and lighter weight compared to fiber-based optical neuroimaging technologies, such as fNIRS and fiber-based HD-DOT. As illustrated in FIG. 6, existing HD-DOT device designs, which incorporate optical fibers as part of the source/detector modules, are typically bulky and heavy. Existing fiber-based HD-DOT devices designed to provide fields of view covering a relatively high proportion of the subject's head, but weigh in excess of 30 lbs. (assuming 1 m fiber length), and even fiber-based HD-DOT devices designed with significantly reduced fields of view are too heavy to be considered wearable in the sense of a bike helmet. Fiber-based HD-DOT device designs (FIG. 6 top left image) typically use "hair-dryer" ergonomics, in which the weight of the fibers, source/detector arrays, and associated structures are externally supported.

In one aspect, the weight of the wearable WHD-DOT device is reduced to a wearable weight of about one pound while increasing the field of view by more than 3-fold, as well as increasing the density of imaging arrays relative to existing device designs, as illustrated in FIG. 6. This enhanced field of view, combined with the increased sensor density may increase the wireless space-bandwidth by 1000-fold and decrease the volumetric point spread function by more than four-fold compared to existing fiber-based device designs, dramatically enhancing the impact of optical neuroimaging methods in the context of various clinical applications.

The WHD-DOT device is well-suited for use in naturalistic neuroimaging techniques. The WHD-DOT device is wearable and capable of performing neuroimaging measurements on a moving subject, unlike fixed scanners, such as fMRI scanners and MEG scanners and fiber-based HD-DOT. The optical signals used by the WHD-DOT device are intrinsically non-ionizing, non-invasive, and enable temporal resolution that is equivalent or better to that of functional MRI techniques.

As described herein, the WHD-DOT device includes a wearable cap provided with a relatively large number of source modules and detector modules. In various aspects, the WHD-DOT device includes up to about 256 sources and up to about 256 detector modules. The design of the WHD-DOT device enables at least several significant advantages over existing systems including, but not limited to, additional control of the sources and detectors, improved source/detector synchronization and the provision of wireless interfaces to the DOT system.

1. WHD-DOT System

FIG. 1 is a schematic overview of a wearable high-density diffuse optical tomography (WHD-DOT) system in one aspect. As illustrated in FIG. 1, the WHD-DOT system includes a WHD-DOT device configured to perform HD-DOT neuroimaging measurements on a subject. As illustrated in FIG. 1, the WHD-DOT device may be operatively coupled to one or more computing devices using any known data interface including, but not limited to, a USB3 interface and a wireless transceiver interface. The computing devices are configured to perform any one of more tasks associated with HD-DOT neuroimaging including, but not limited to, signal encoding, signal decoding, image reconstruction, image analysis, and any other tasks associated with HD-DOT neuroimaging.

Detailed descriptions of the elements of the WHD-DOT device and associated computing devices are provided below.

a) WHD-DOT Device

Figure 7:
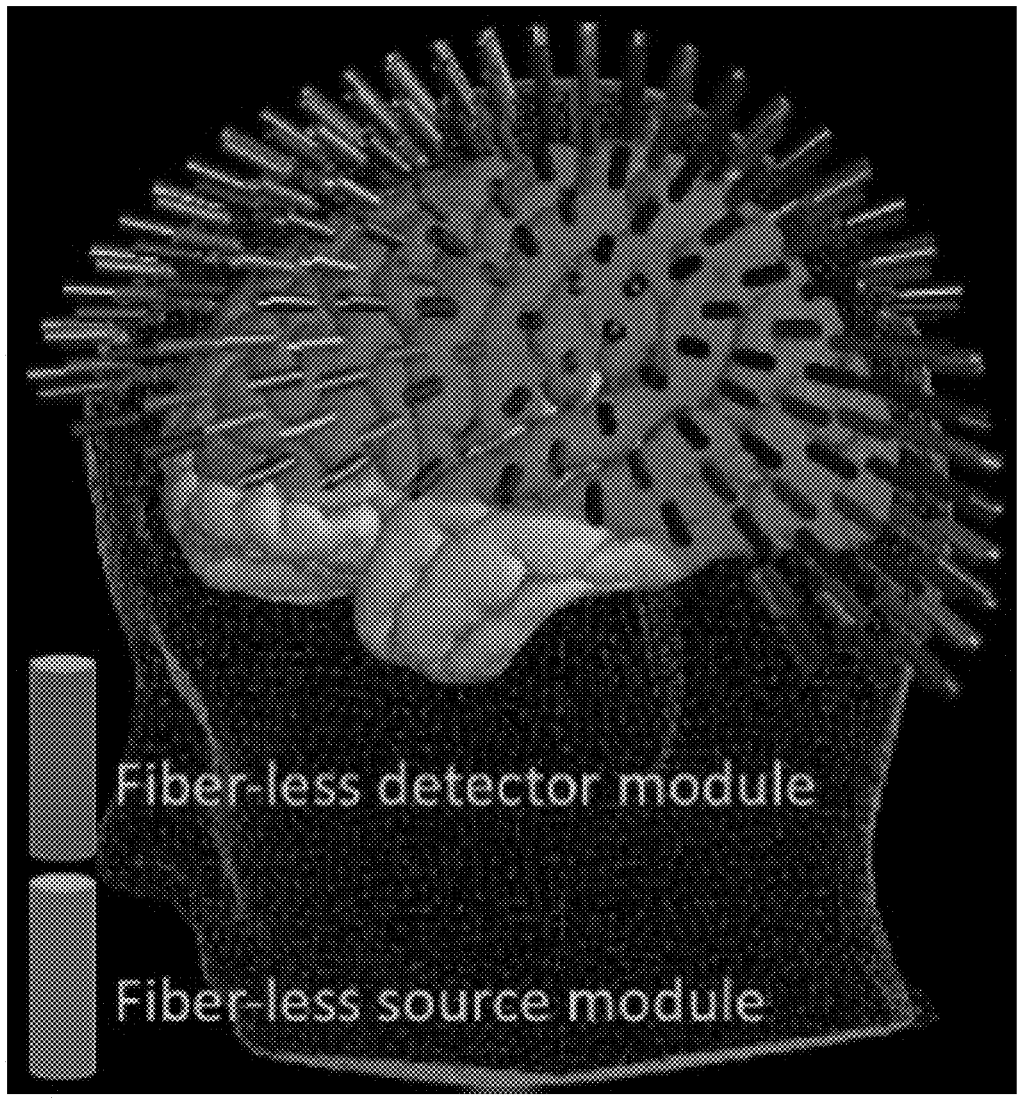
FIG. 7 is a schematic diagram of a wearable WHD-DOT instrument in accordance with one aspect of the disclosure.

FIG. 7 is an image illustrating the elements of a WHD-DOT device configured to obtain measurements for HD-DOT neuroimaging in one aspect. In various aspects, the WHD-DOT device may include a flexible cap supporting a plurality of source modules and a plurality of detector modules arranged in an array. The array of source and detector modules is distributed over a field of view positioned over at least a portion of the subject's scalp overlying at least a portion of the subject's brain cortex to be imaged using the WHD-DOT system. In addition, as illustrated schematically in FIG. 1, the WHD-DOT device may further include a main board operatively coupled to the plurality of source modules and detector modules, as well as in communication with one or more computing devices. The main board is further configured to be worn as part of the WHD-DOT device along with the plurality of source and detector modules.

In one aspect, the WHD-DOT device may include as many as 256 source modules and 256 detector modules or more. In this aspect, each source module and each detector modules may be packaged in a housing with dimensions ranging in size from 5 mm in maximum width and 20 mm in length to as small as about 3 mm maximum width and about 10 mm length. Importantly, this form factor is needed to act as a brush to brush through the hair and create contact with the scalp. The plurality of source and detector modules may be integrated into a wearable, flexible cap configured to maintain the arrangement of the source and detector modules against the subject's scalp, as well as to enhance the contact of each source and detector module against the scalp. In this aspect, the WHD-DOT device may be powered using a battery that could either be integrated into the cap, or contained in a small back pack wearable by the subject to provide power sufficient to enable an HD-DOT imaging session. By way of non-limiting example, a battery weighing about 1 lb. with a capacity of about 120 W-hr is capable of powering the WHD-DOT device for imaging sessions of up to about one hour. In various aspects, the WHD-DOT device may be powered using higher capacity batteries or other power sources to enable HD-DOT imaging sessions in excess of one hour. In various other aspects, the duration of imaging sessions enabled by a battery may be extended by reducing the power requirements of the WHD-DOT device by refining the design. In one aspect, the reduced energy demand of the WHD-DOT device is enabled using the incorporation of higher-efficiency components including, but not limited to, control modules (FPGAs), light sources, and light detectors. In another aspect, the reduced energy demand of the WHD-DOT device is enabled by altering the architecture of the WHD-DOT device including, but not limited to, altering the number or arrangement of laser sources and light detectors, altering the interconnections of various elements of the WHD-DOT device, and altering the degree of local data processing and/or local control of the operation of device elements.

In various aspects, the design features of the WHD-DOT device maintain the advantages of existing fiber-based HD-DOT devices described above, while enabling the capability to perform high-quality neuroimaging on moving subjects, making possible high-resolution neuroimaging of subjects with motor system disorders such as cerebral palsy. In various aspects, the design features of the WHD-DOT device are configured to enhance the device's wearability, signal-to-noise performance, and resolution. In various other aspects, one or more electrical elements of the WHD-DOT device are selected based on at least one performance characteristic of the system, including, but not limited to: enhanced noise equivalent power (NEP), enhanced detectivity (Det=NEP/area), enhanced dynamic range (DNR), reduced cross-talk (CT), increased frame rate (FR), and enhanced coupling of the source and detector modules to the scalp of the subject. In additional aspects, the WHD-DOT device provides for the implementation of signal modulation/demodulation strategies for encoding source illuminations, as described below.

In various aspects, the neuroimaging performance of the WHD-DOT device is enhanced by various arrangements of the electrical elements of the device. In one aspect, the signal-to-noise performance is enhanced by mounting the TIA and ADC of the detector module as close as possible to the detector, as described in detail below. In addition, the electronics of the detector module are reduced in size, power consumption, and weight to enable a functional wearable WHD-DOT headset with minimal cabling due to the elimination of optic fibers. Additionally, the electronics of the WHD-DOT device are positioned out on the subject's head to enable synchronization of the source and detector control. To enhance mobility of the WHD-DOT device, a portable, wearable battery pack may be used to power the WHD-DOT device for up to an hour or more of data acquisition.

In various aspects, the design of the WHD-DOT device includes various design features that impact the weight, performance, patient mobility, and battery life of the WHD-DOT device. In some aspects, the connectivity of the of the WHD-DOT device to the stationary computing devices is enabled using any known suitable technology including, but not limited to, a wired interface, such as a USB3 interface, and a wireless interface, such as a wireless transceiver. Without being limited to any particular theory, the wired interface is accompanied by reduced power requirements but with patient mobility limited by cable length, whereas the wireless interface enhances patient mobility but with higher power usage.

In other aspects, power is supplied to the WHD-DOT device using any known suitable power supply including, but not limited to, a stationary power supply, such as a power converter operatively coupled to a stationary power outlet, and a mobile power supply, such as a battery. Without being limited to any particular theory, it is thought that the stationary power supply is capable of providing power to the WHD-DOT device effectively indefinitely but with reduced patient mobility due to the required power cable, whereas the battery is capable of providing power for a limited time but with enhanced patient mobility because the battery is carried by the patient, eliminating need for a power cable to a stationary power source. In one aspect, the battery is incorporated into the portion of the WHD-DOT device worn on the patient's head or is provided in the form of a separate wearable element including, but not limited to, a backpack, connected via a power cable to the portion of the WHD-DOT device worn on the patient's head. Without being limited to any particular theory, the incorporation of the battery into the portion of the WHD-DOT device worn on the patient's head is thought to enhance electrical efficiency, to reduce the overall weight of the WHD-DOT device, and/or to enhance patient mobility, but is further thought to limit battery life due to battery at the expense of reduced battery life. Although a higher-capacity battery may be provided in the form of a backpack to extend battery life, the added weight, power cable, and backpack may hinder movement of the patient, and the efficiency of the WHD-DOT device may be reduced due to the losses associated with the added power cable and electrical connections.

In additional aspects, the selection of the control module (FPGA) of the WHD-DOT device may vary based on any one or more of at least several factors including, but not limited to, device performance, device weight, battery life, and any other relevant factor without limitation. In one aspect, the control module (FPGA) is located on the portion of the WHD-DOT device worn on the patient's head or the control module (FPGA) is located remotely in a location including, but not limited to, within another wearable portion of the device such as a backpack or at a stationary position such as within one or more stationary computing devices. In another aspect, the WHD-DOT device includes multiple control modules (FPGAs) located in the portion of the WHD-DOT device worn on the patient's head and/or remotely located. Without being limited to any particular theory, it is thought that locating one or more control modules (FPGAs) on the portion of the WHD-DOT device worn on the patient's head enhances device computing speed and electrical efficiency by reducing the coupling elements associated with data transfer to the computing devices, but increases the size and weight of the head-worn portion of the device. However, computing speed may be enhanced by the inclusion of faster and/or multiple control modules (FPGAs) within the computing devices to enhance computing speed as limited by data transfer rates from the WHD-DOT device. In some aspects, the DOT signals obtained using the WHD-DOT device are processed locally on the device and transmitted to a computer wirelessly, further reducing weight and device performance.

1) Flexible Cap

In various aspects, the WHD-DOT device includes a plurality of source and detector modules coupled to a flexible, layered cap, resulting in a "smart brush" arrangement where each brush tip contains either a detector module or a source module, as illustrated in FIG. 7. In one aspect, the isolated source and detector modules are incorporated into an anatomically designed cap configured to flexibly adapt to two axes of curvature to conform to each individual subject's head surface. In this aspect, the "smart brush" arrangement of the source modules and detector modules enable these elements to comb through the subject's hair and make intimate contact with the scalp to send and receive light signals. This "smart brush" arrangement, adapted from the fiber-based existing HD-DOT device design (see FIG. 5A), adapts the support elements, previously used to stably press fiber bundles against the subject's scalp, to enable the stable support of the source and detector modules against the subject's scalp. The stable scalp/module coupling, dense spatial sampling and entire scalp coverage enabled by the flexible cap and "smart brush" arrangement enhance light collection efficiency and resulting image resolution performance. In various aspects, the cap design may be customized to an individual subject using an anatomical computer model to optimize the placement of sources and detector modules to accommodate the position dependent curvature of the head surface.

Figure 14A:
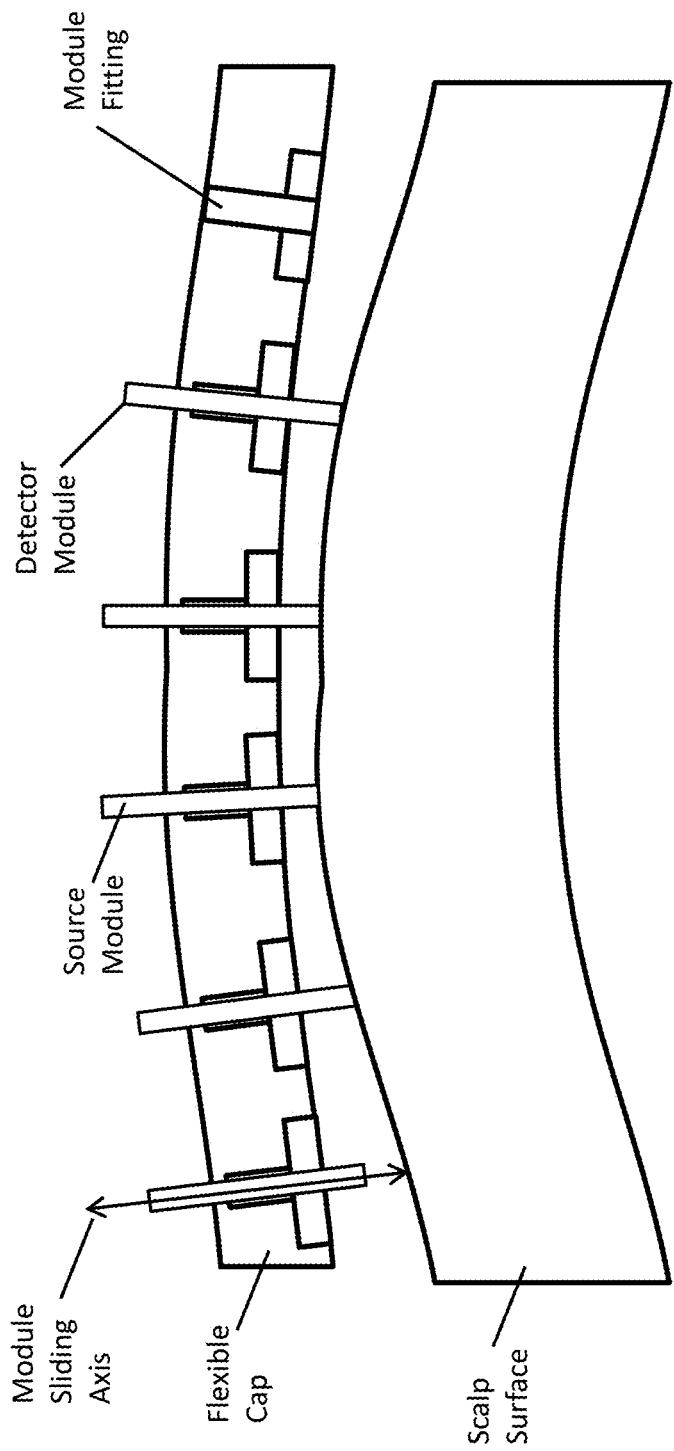
FIG. 14A is a cross-sectional view of a section of a flexible cap with embedded module fittings and source and detector modules coupled to the module in accordance with one aspect of the disclosure.

FIG. 14A is an illustration of a flexible layered cap of the WHD-DOT device in one aspect. As illustrated in FIG. 14A, the flexible layered cap includes a plurality of modified top-hat shaped sleeves defining a module fitting configured to receive a source module or a detector module and to maintain the source module in position within the source/detector array, and to further maintain each module in contact with the scalp of the subject. As illustrated in FIG. 14A, the module fittings receive each source/detector module in a sliding arrangement to allow for vertical compliance, but maintain lateral stability. The vertical compliance further provides for individual positioning of each module against an uneven scalp surface by sliding along the vertical sliding module axis.

In some aspects, the fit of the WHD-DOT device may be assessed by obtaining preliminary DOT measurements once the WHD-DOT device is fitted to the subject prior to acquiring neuroimaging data. In one aspect, the WHD-DOT system may be configured to display information representative of DOT signal quality during fitting of the flexible cap of the WHD-DOT device to the scalp of the subject. In one aspect, real-time displays in both "measurement space" and as well as image space may be generated using a computing device (CPU, GPU, FPGA or microcontroller), and the estimates of real-time imaging performance may be used to guide the fitting of the WHD-DOT device to the subject within 1 minute of initial cap placement.

ii) Detector Modules

Referring again to FIG. 7, the WHD-DOT device includes a plurality of detector modules. In one aspect, the detector modules have an elongate form factor, in which the detector modules are oriented perpendicular to the head surface and may consequently function as combs to penetrate the subject's hair and to further provide enhanced optical coupling to the subject's scalp tissue. In various aspects, the elongate form factor may be characterized by a fineness ratio (length/maximum width) ranging from about 0.2 to about 30.

In another aspect, the isolated detector modules are incorporated individually into an anatomically designed cap configured to flexibly adapt to two axes of curvature to conform to the subject's individual head surface, further enhancing optical coupling. In an additional aspect, the smaller size, lighter weight and lower power requirements of the detector modules render the WHD-DOT device wearable with relatively few or no cables connected to other devices of the WHD-DOT system.

In various aspects, the detector modules may have any form factor without limitation characterized by the fineness ration described above. The form factor of the detection modules may have any cross-sectional profile without limitation, including a rounded cross-section such as circular or elliptical, a polygonal cross-section such as triangular, square, octagonal, and the like, or any other suitable cross-sectional profile. In various other aspects, the form factor of the detector modules may have uniform or non-uniform cross-sectional profiles with respect to both size (i.e. taper) and shape. In various additional aspects, the detector modules may further include additional surface features including, but not limited to, notches, windows, openings, electrical connectors, optical connectors, and the like.

In various aspects, the dimensions of the detector modules are selected to enhance the integration and performance of the detector modules within the WHD-DOT device. In one aspect, the design of the detection module enables a low detectivity threshold. Detectivity, as used herein, is defined as roughly equal to the noise equivalent power of the detector divided by the detector's sensor area. To reduce weight of the WHD-DOT device while maintaining large detection area ($\sim 6$ mm$^2$), large field of view ($\sim 500$ cm$^2$) and dense spatial sampling ($\sim 1$ cm), the detector modules are positioned onto the head. For stable coupling to the head, the form factor of the detector modules function as a comb penetrating through the hair of the subject, imposing an upper limit of about 6 mm$^2$ per detection module area in some aspects. In one aspect, the detection modules have a sensor area ranging from about 1 mm² to about 6 mm². In various other aspects, the detection modules have a sensor area ranging from about 1 mm² to about 2 mm², from about 1.5 mm² to about 2.5 mm², from about 2 mm² to about 3 mm², from about 2.5 mm² to about 3.5 mm², from about 3 mm² to about 4 mm², from about 3.5 mm² to about 4.5 mm², from about 4 mm² to about 5 mm², from about 4.5 mm² to about 5.5 mm², from about 5 mm² to about 6 mm². In an exemplary aspect, the detection modules have a sensor area ranging from about 2 mm² to about 3 mm². Further, for stable coupling to the head, each source and detector module of the array may be mechanically isolated to enable conformal contact of the array with the head surface.

In various aspects, housings may be selected for use as both the source modules and the detector modules. The detector modules are positioned in an array arrangement on a head-conforming flexible head cap. Each detector module may be coupled to the head-conforming flexible head cap using top hat-shaped barrel fittings with cross-sectional profiles matched to the corresponding cross-sectional profiles of the source and detector housings, and configured to receive each detector module and source module in a sliding arrangement, as illustrated in FIG. 14A. In one aspect, the sliding arrangement of sources and detector modules with barrel fittings enable individual conforming of the source and detector module fittings to the head surface. In other aspects, the cross-sectional shape of the housing of the detector module may be any suitable piston shape including, but not limited to, rectangular, triangular, or any other suitable cross-sectional shape without limitation.

Figures 13A, 13B, 13C:
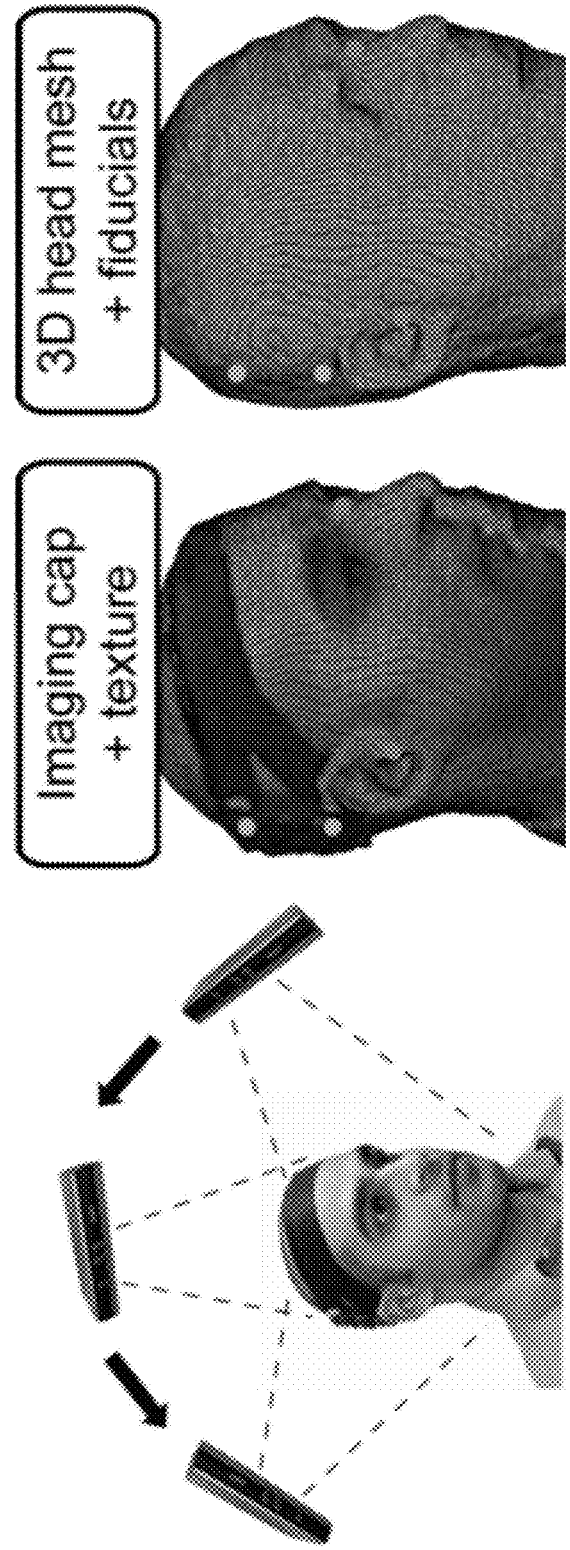
FIG. 13A is a schematic diagram showing the operation of a Kinect camera configured to provide real-time 3D object scanning of a head of a subject.
FIG. 13B is an image of a texture map of the subject wearing the imaging cap used to determine the position of anatomical landmarks (red dots) as well as cap fiducials (blue dots) obtained using the Kinect camera as illustrated in FIG. 13A.
FIG. 13C is an image of a 3D head surface model of the subject with mapped anatomical landmarks (red dots) as well as cap fiducials (blue dots) obtained using the Kinect camera as illustrated in FIG. 13A.
Figure 14B:
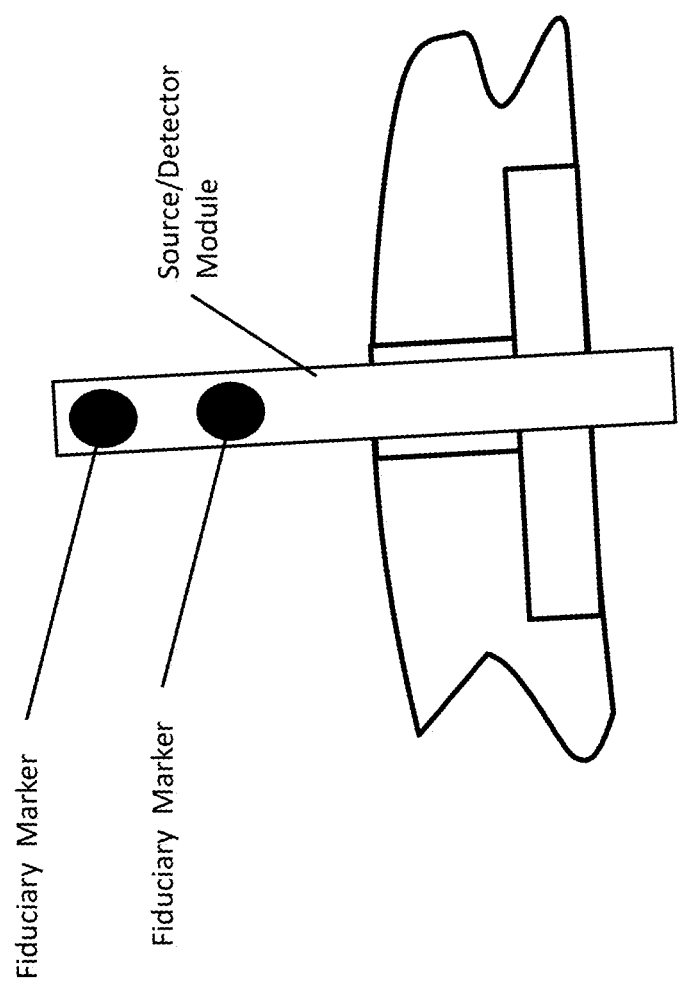
FIG. 14B is a cross-sectional view of a section of a flexible cap with embedded module fittings and source and detector modules coupled to the module in accordance with one aspect of the disclosure.

Referring to FIG. 14B, the housings of the source and detector and source modules may further include a pair of fiducial markings to uniquely identify at least one of: the position of the detector or source module and the orientation of the housing relative to the scalp of the subject. Without being limited to any particular theory, the pair of fiducial markings is compatible with a face tracking algorithms that may be used to define the positions and orientations of the source and detector modules with respect to the scalp of the subject, as described herein and illustrated in FIGS. 13A, 13B, and 13C.

In various other aspects, the fiducial markings may be provided in any suitable form including, but not limited to, cross-hairs, dots or other shapes, rings around the circumference of the detector/sensor module housing, and any other suitable format. In various aspects, the housing may include two spaced fiducial markers to provide a minimum definition of the position and orientation of the housing, but three, four, five, or more fiducial markers may be included to provide redundancy, to encode the identity of the individual source or detector within the housing, or to enable viewing from different camera positions.

In one aspect, the maximum width of the detector module ranges from about 1 mm to about 6 mm, the length of the detector module ranges from about 10 mm to 30 mm, and the volume of the photodiode detector module (PDM) ranges from about 10 mm³ to about 180 mm³. In another aspect, the dimensions of the detector modules further enable the distribution of modules characterized by a nearest-neighbor spacing ranging from about 6 mm to about 20 mm. In one aspect, the form factor of the source and detector modules may have maximum widths in the range of 1 to 25 mm and lengths in the range of 10 mm-30 mm.

In one aspect, the source and/or detector modules use small light pipes to relay light to and from the scalp surface. These light pipes may be made out of plastic, or glass, with either no-cladding or with cladding based on standard fiber optic design principals. The cross-sectional areas of the light pipes may be smaller or bigger than the source or detector modules. Light pipes with smaller maximum widths maybe chosen to optimize the combing action through the hair. Light pipe maximum widths larger than the optode modules maybe used to control the collection angle for detection, or the illumination angle for sources. The light pipes may have cross-sectional profiles of any shape without limitation including circular, elliptical, or polygonal shapes such as triangular, square, octagonal, and the like. The lengths of the light pipes can be optimized for, combing through hair, light transmission, expansion of effective illumination/detection area, and other cap design criteria.

Figure 2:
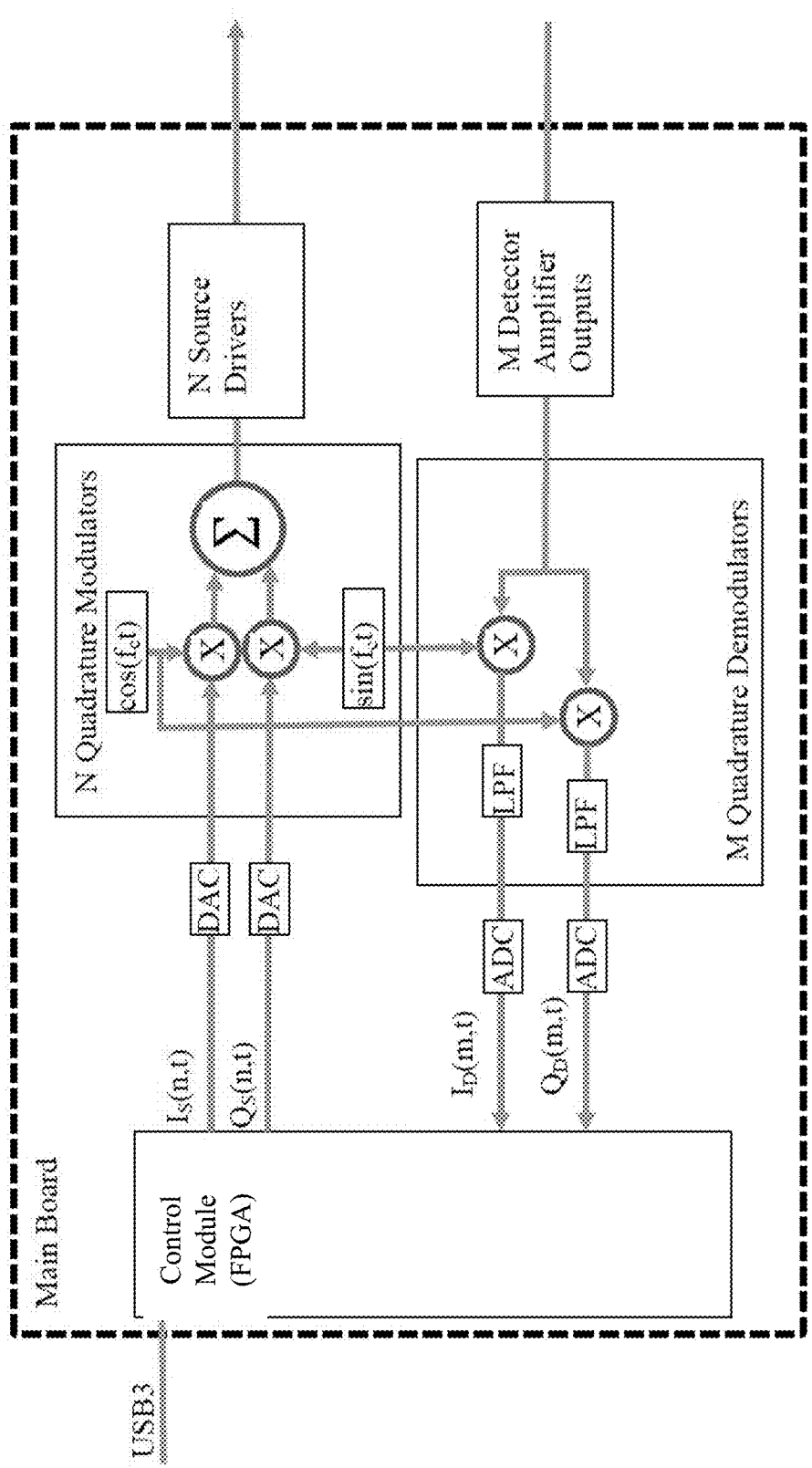
FIG. 2 is a schematic diagram of a main board of an HD-DOT instrument, including a quadrature modulation circuit and source drivers in accordance with one aspect of the disclosure.

Referring again to FIG. 8B, each detector module includes a photodiode, a Transimpedance Amplifier (TIA) and an Analog to Digital Converter (ADC) and a housing. In various aspects, any one or more of the photodiode, Transimpedance Amplifier (TIA) and Analog to Digital Converter (ADC) may be contained within the housing. The housing is configured to replicate the mechanics of the fiber bundles in the imaging cap of existing fiber-based HD-DOT device designs. Referring to FIG. 1, the ADC acquires the signal from the TIA output and is controlled by the control module on the main board. In various aspects, the control module may be any suitable electrical component without limitation. Non-limiting examples of electrical components suitable for use as the control module include microcontrollers, central processing units (CPUs), and field programmable gate arrays (FPGAs). In one aspect, the control module is an FPGA, as illustrated in FIG. 1 and FIG. 2.

Referring again to FIG. 1, the TIA output acquisition is synchronized with the source control by the control module (FPGA) in some aspects. In an aspect, the PDM channel (PD+TIA+ADC) has a very low power consumption (10 mA @18V+4 mA@-18V=250 mW/channel) thereby enabling up to an hour or more of data acquisition using a wearable battery pack to support tether-less and free walking WHD-DOT imaging.

In one aspect, the ADC of the detector module communicates with the control module (FPGA) of the main board, described below, through a 4 wire SPI digital interface. This 4 wire SPI digital interface is controlled by a control module (FPGA). In various alternative aspects, additional control lines are included to switch the gain of the TIA and/or to vary the power of the sources to optimize SNR and frame rate.

In another aspect, the small form factor circuitry of the detector module enables extremely low capacitance (15 pF) at 12V reverse bias. This reduction in capacitance reduces the input referred voltage noise for a given bandwidth of the TIA. Using this detector module and control module (FPGA) combination, the imaging performance of the WHD-DOT device is met or improved, compared to existing HD-DOT devices that use APD detection. By way of non-limiting example, one detection module may have an NEP=47 fW/√Hz, with a 7.7 mm detector area, corresponding to a DET=6.1 fW/√Hz-mm². While the NEP of the detection module is about 2× higher than the APD in this non-limiting example (Hamamatsu C12703-01, with NEP=20 fW/√Hz), the APD has a smaller collection area and requires a fiber bundle with 50% packing fraction, yielding a DET=10 fW/√Hzmm². In another aspect, the detection module detectivity is designed to be lower than the corresponding detectivity of the APD module.

Photodiodes

Existing HD-DOT systems make use of avalanche photodiodes to achieve low noise floors. However, the sensor volumes of avalanche photodiode modules (APDM) used in existing HD-DOT devices are typically too large to mount directly to the head and require use of fiber-bundles. The lowest noise APD's modules available, and commonly used in existing fiber-based HD-DOT devices (Hamamatsu C12703-01 or equivalent) have an NEP=20 fW/√Hz. Accounting for light collection area, these APD modules are typically used with 2.5 mm fiber bundles that have a 50% packing fraction yielding a detectivity of about 10 fW/√Hz-mm². In various aspects, the design of the detector modules of the WHD-DOT device is selected to enable a detectivity that is matched to the detectivity of about 10 fW/√Hz-mm² typical of existing fiber-based HD-DOT devices.

The use of APDs in existing fiber-based HD-DOT sensors further require significant support electronics that add to the sensor's bulk, including 100V DC-DC power converters and temperature stabilization, due to the highly temperature-dependent gain of typical APDs. By way of non-limiting example, the Hamamatsu C12703-01 modules are about the size of a pack of cards (56 mm×88 mm×10 mm~50,000 mm³).

However, the factors limiting the size reduction of photo-diodes (PD) lie not with the NEP of the PD in isolation. Some existing PD devices have lower NEP specifications than the C12703-01 APD modules described above. In various aspects, the design of the WHD-DOT device enhances signal-to-noise by incorporating lower noise TIAs afforded by recent advances in CMOS components, thereby permitting the use of higher-noise PD devices other than APDs while maintaining a low noise floor. In addition, the detector modules of the WHD-DOT device incorporate reduced-size TIAs, ADCs, and PDs, thereby lowering capacitance throughout the TIA circuits and further lowering noise floors.

Any photodiode with sufficiently low NEP and capacitance within the size ranges described above may be selected for use in the detector modules without limitation. In various aspects, the photodiodes of the detector modules may be selected from the group consisting of Hamamatsu S5971 (1.13 mm²) and the Hamamatsu S12158-01CT (7.7 mm²). In one aspect, the Hamamatsu S12158-01CT photodiode is used as the photodiode for the WHD-DOT device. This chip uses a small form factor Chip on Board (COB) package which includes the die with minimal additional packaging. This provides the reduced-size Si-PD package with a small active area (7 mm²).

TIA

In various aspects, the TIA of the detector module is selected to meet the low noise performance requirements. In one aspect, the TIA may be characterized as comprising a 50 KHz bandwidth. In one aspect, the detector module may include a TI OPA1652 op amp with a 30 M feedback resistor with a +/−18V supply.

In one aspect, the trans-impedance amplifier (TIA) may be a Texas Instruments OPA Operational Amplifier (OpAmp). Due to the absence of the solid-state gain associated with the APDs used in fiber-based systems, the input referred noise of the TIAs selected for use in the detector module of the WHD-DOT device is selected to be lower since the PD output is lower. In various aspects, advances in OpAmp noise performance have enabled lower input capacitances (e.g. 5 pF) which reduce the input referred voltage noise. In various aspects, the front end of this Op-amp may include, but is not limited to, one of: BJT, JFET or CMOS amplifiers. In an aspect, a CMOS amplifier is used, because noise may depend on both voltage noise and current noise. Although BJT amps have better 1/f noise, the signal in the disclosed WHD-DOT system is modulated at 10 kHz. Although JFET amps are better for low voltage noise, JFET amps are less effective for current noise. In one aspect, the TIA is selected to be an OPA OpAmp (see FIG. 8B), which is characterized by a small package (3×3×1 mm) and a wide supply range which enables the use of a large reverse bias voltage on the PD, and further enables reduction of the input capacitance.

ADC

In previous fiber-based HD-DOT devices, dedicated ADC's were used for each detection channel. The ADC chips of previous fiber-based HD-DOT devices, for example, the AK5394A by Asahi Kasei, were originally designed used in commercial direct-to-disc audio recording instruments and had dimensions 18.7×10×2 mm (volume=374 mm3). Operating at 96 kHz the AK5394A chips had 18 effective number of bits (ENOB) and was essentially transparent to the analog circuitry (APD module). ADC's with reduced size may also be selected in some aspects. In various aspects, recent advances in shrinking the size of ADC's and support circuitry are leveraged in the design of the WHD-DOT device.

In one aspect, the detector module of the WHD-DOT device may include a 16 bit ADC, including, but not limited to, a Maxim MAX11166. The Maxim MAX11166 ADC is a true 16 bit converter with +/−5V input swing and a maximum sample rate of 500K Samples/sec. in various aspects. When decimated down to 96 ksps this ADC achieves 18-bit ENOB. The ADC chip has dimensions 3×3×1 mm (volume=9 mm3), representing a dramatic 50-fold reduction in size compared to the AK5394A chips used in previous fiber-based HD-DOT devices.

iii) Source Modules

In various aspects, the WHD-DOT device includes a plurality of source modules coupled to the flexible cap, as described above in FIG. 8B and FIG. 14A. In various aspects, the source module includes a light source positioned within a housing with dimensions matched to those of the plurality of detector modules. Non-limiting examples of suitable light sources include LEDs, lasers or VCSELS. In various aspects, source drivers configured to drive the sources may be positioned within the source module housing along with the LED/laser or on the Main Board as shown in FIG. 1. In one aspect, the source modules are driven by source drivers included on the main board and controlled by the control module (FPGA) (see FIG. 1). In one aspect, the sources may be mounted in small form factor cylinders (e.g. about 3 mm maximum width and about 10 mm length), enabling a similar manner of coupling the source modules to the head using the flexible cap as was described for the detector modules above.

Each source module is configured produce light at one or more suitable wavelengths without limitation. The wavelength of light produced by the source modules may be selected based on at least one factor including, but not limited to, penetration depth through the intervening tissues of the subject's scalp, skull and brain, selective absorption or transmission by structures within the subject, such as oxygenated red blood cells, deoxygenated red blood cells, melanin, and exogenous contrast agents. Non-limiting examples of suitable wavelengths produced by the source modules includes one or more in the range of 650 nm-1300 nm.

In one aspect, each source module may produce a single wavelength of light. In another aspect, all source modules may produce the same wavelength of light. Alternatively, a first portion of the source modules may produce the same first wavelength and an additional portion of the source modules may produce the same additional wavelength different from the first wavelength. In an additional aspect, the same source module may produce two or more different wavelengths. By way of non-limiting example, the source module may include a small package, dual wavelength LED's from Epitex (L750-850-04A, AlGaAs, dual wavelength 15 mW @750 nm and 18 mW @ 850 nm). In one aspect, the LED may be a small package, dual wavelength LED from Epitex (L750-850-04A, AlGaAs, dual wavelength 15 mW @750 nm and 18 mW @ 850 nm).

iv) Main Board

In various aspects, the circuitry for operating the source and detector modules are fully positioned on the head of the subject within the flexible cap as described above (see FIG. 1), are free of fiber coupling, and consequently overcome at least one or more disadvantages of existing HD-DOT devices. In various aspects, this circuitry may be included in a main board of the WHD-DOT device.

In various aspects, the main board may be configured to perform at least a portion of the tasks associated with HD-DOT imaging including, but not limited to operating the source modules and detector modules as described above, performing signal encoding and decoding, and performing image reconstruction. As illustrated in FIG. 1, the main board of the WHD-DOT device may include a plurality of source drivers configured to operate the plurality of source modules, a controller including, but not limited to, an control module (FPGA) configured to control the operation of the plurality of source modules and detector modules, and one or more data ports including, but not limited to, and at least one data port coupled to one or more computing devices including, but not limited to a USB3 interface and a wireless transceiver interface.

In various aspects, the main board may include circuit elements configured to perform varying degrees of the processing associated with the HD-DOT imaging methods described herein. In one aspect, the main board may be configured to operate the source modules, to receive raw data from the detectors, and to stream the raw detector data to a separate computing device without further processing. In another aspect, the main board may be further configured to locally process the detector data and to stream the processed data to the separate computing device.

In various other aspects, the main board may stream data to a separate computing device using any data communication device without limitation including, but not limited to, a USB3 data connection and a wireless data connection, described in additional detail below.

The driver circuit now available is also small (3 mm×4.9 mm). The design and performance of this may be carried over directly from the previous HD-DOT which used LED's with similar powers and wavelengths.

Control Module

In various aspects, the main board includes at least one control module configured and programmed to communicate with a separate computing device and to control the operation of the source and detector modules, as well as to optionally enable one or more additional methods associated with DOT neuroimaging as described below. In one aspect, the source and detector modules are connected by flex circuits to one or more control modules that include wireless data connectivity to a separate computing device. As described above, the control module may be any suitable electrical component without limitation. Non-limiting examples of electrical components suitable for use as the control module include microcontrollers, central processing units (CPUs), and field programmable gate arrays (FPGAs). In one aspect, the control module is an FPGA, as illustrated in FIG. 1 and FIG. 2.

In various aspects, the any suitable control module device may be included on the main board of the WHD-DOT device without limitation. The control module device may be selected based on at least one of a plurality of factors including, but not limited to, the amount of local processing to be performed by the main board, the number of data ports associated with source modules and elements of the detector modules, size of the FPGA device, processing speed of the FPGA device, data communication requirements, and any other suitable factor without limitation.

In one aspect, the FPGA may be provided in the form of a Xilinx Artix-7 FPGA on an Opal Kelly XEM7310-A75 FPGA Development Board. The FPGA in this aspect enables a relatively large I/O count (160 lines) sufficient to steam data from at least 96 detection channels, control at least 96 source modules, has low power consumption of about 3.5 W and has a small size (7.5×5×1.6 cm). In another aspect, the FPGA may be provided in the form of an Opal Kelly XEM6310 board with a Xilinx Spartan 6 xc6x1s150 FPGA. In this other aspect, the board includes a USB3 interface, a 100 MHz clock, 120 pins of digital I/O, and a size of 50 mm×75 mm. In this other aspect, the FPGA generates control signals to synchronously sample the ADCs of the detector modules at up to 500 KSamples/sec, as well as generating control signals to operate the source drivers.

Wi-Fi streaming at 500 Mbps to a host computer may be provided by an Intel compute stick (Intel, STK2 M3W64CC, size 11.4×3.8×1.2 cm). Additional control lines could be used to switch the gain of the TIA to vary the power of the sources. In an aspect, the Front Panel Software Development Kit (SDK) is used to communicate with the FPGA to simultaneously stream data from the ADCs to the computer and the source pattern data from the computer to the source drivers. Decimation and compression can be implemented on the FPGA to reduce traffic over the USB bus. Three FPGA/Wi-Fi modules may support the full 256 detector, 256 source system.

In one aspect, the FPGA may be configured and programmed to acquire ADC output from the detector modules in coordination with the operation of the source modules. In various aspects, the acquisition may be synchronized with the source control. This synchronization of the operation of the source and detector modules may enable data encoding and decoding used to associate acquired detector data with a particular detection channel. As used herein, a detection channel refers to a particular source module-detection module pair configured to obtain DOT measurements in a particular region of the subjects brain. Each detection channel may include a source module and any one of a plurality of neighboring detector modules positioned in sufficiently close proximity to the source module.

In various aspects, the FPGA may operate the source modules and detector modules to enable at least one or more encoding methods. Encoding methods, as referred to herein, refer to methods of operating the source and detector modules in a coordinated sequence so that each detector signal received from each detector module may be associated with a unique detector channel. Because each detector channel is associated with a unique location on the brain of the subject, the encoding methods enable spatial mapping of the detector signals that serves as a starting point of DOT image reconstruction.

Any one or more encoding methods may be enabled by the FPGA module including, but not limited to, temporal encoding, spatial encoding, and frequency encoding. Temporal encoding, as used herein, refers to acquiring data from each detector channel at a separate time from any of the other detection channels. Spatial encoding, as used herein, refers to acquiring data from two or more detector channels separated at a distance sufficient to eliminate cross-talk between the two or more detection channels. Frequency encoding, as used herein, refers to operating each source according to a frequency modulation scheme and processing each detector signal according to a frequency demodulation scheme, in which each source module is associated with an encoding frequency used to identify the detection channel for each received detection signal.

In one aspect, the FPGA may operate the source modules and detector modules to enable temporal and spatial encoding methods. In one aspect, for sub-arrays of 4×4 detectors interlaced with 4×4 sources (see FIG. 7), 16-step time encoding of the sources is used. In this aspect, the full cap, which includes a plurality of source and detector modules forming multiple 4×4 sub-arrays, all sub-arrays may be run concurrently since the activated sources at any given time are separated by a distance that is at least twice the longest usable source-detector pair (5th nearest-neighbor) distance, thereby prevent cross-talk between detector channels. In various aspects, the FPGA may operate the source modules and detector modules at frequencies less that about 300 kHz to enable temporal and spatial encoding methods.

In another aspect, the FPGA may operate the source modules and detector modules to enable frequency encoding methods. In one aspect, the frequency encoding method includes quadrature modulated the source modules, enabling data acquisition bandwidths of at least 50 MHz FIG. 2 is a schematic illustration of a main board configured to enable frequency encoding in one aspect. As illustrated in FIG. 2, DACs and at least one quadrature modulation circuits may be installed between the FPGA and the source drivers in this aspect to enable quadrature encoding of source module signals. In addition, at least one quadrature demodulation circuit and ADCs may be installed on the main board between the detector module output signals and the FPGA as shown in FIG. 2 to enable quadrature decoding of source module signals.

In various aspects, the modulation/demodulation may be enabled using software, firmware or hardware on the FPGA. The modulated signal is then connected to a DAC with a suitably high sample rate for the wide bandwidth system which in turn drives the source drivers. The DAC and source drivers can either be on the main board or preferably, on the head. Similarly, the detector output can be connected to an ADC with a suitably high sample rate for the wide bandwidth system. The ADC can either be on the main board or preferably, on the head. In one aspect, raw data may stream from the FPGA to a separate computing device for demodulation offline. In various aspects, demodulation of the detector signals may be enabled using software, firmware or hardware on the FPGA. In various aspects, the wider bandwidth and modulation of signals using frequency encoding provides for the detection of both amplitude (intensity) and phase of the detected signals.

II. Computing Systems and Devices

Figure 15:
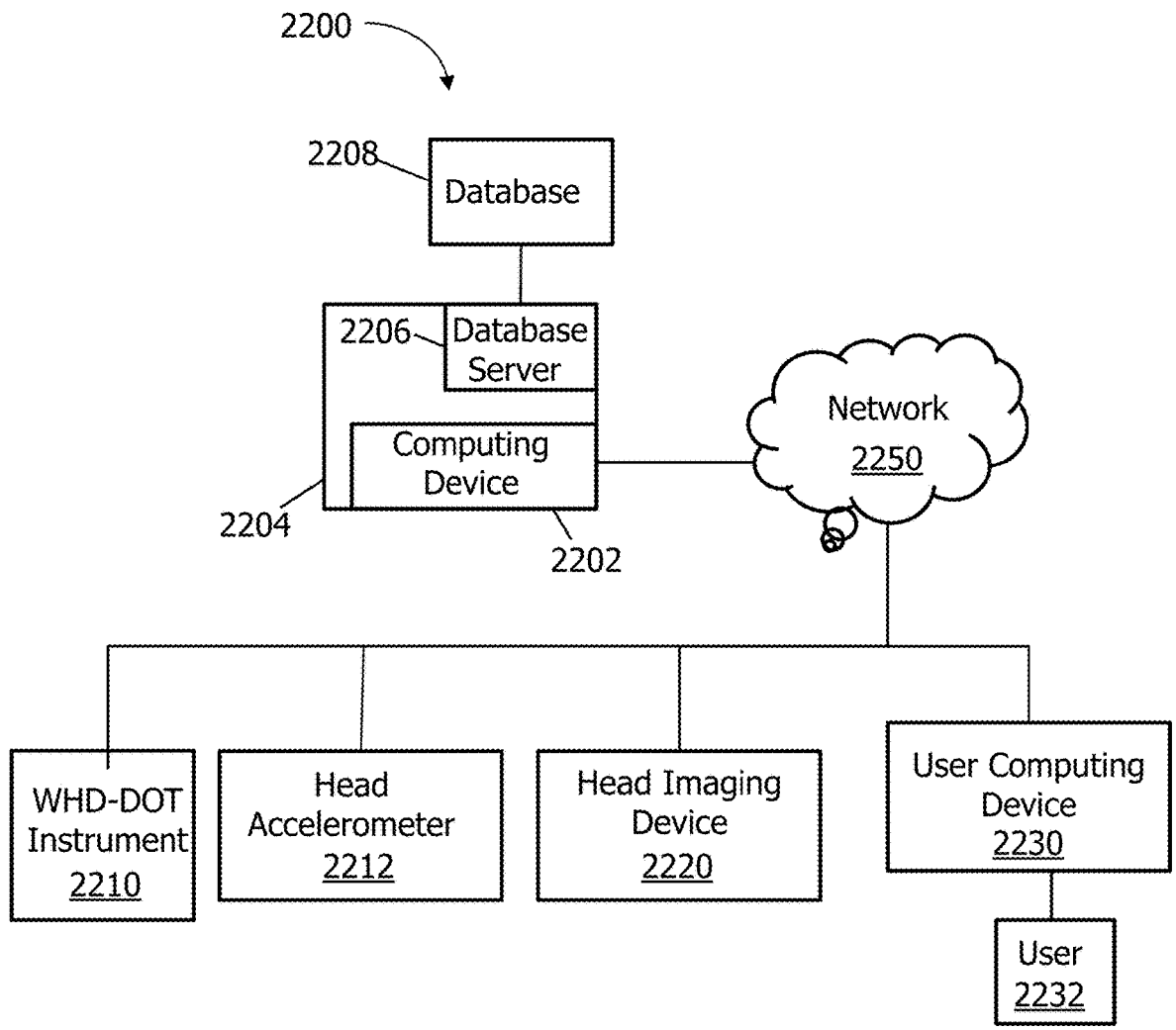
FIG. 15 is a block diagram schematically illustrating a WHD-DOT system in accordance with one aspect of the disclosure.

FIG. 15 depicts a simplified block diagram of a computing device 2200 for implementing the methods described herein, similar to the computing devices shown in the WHD-DOT system illustrated in FIG. 1. As illustrated in FIG. 15, the computing device 2200 may be configured to implement at least a portion of the tasks associated with HD-DOT imaging using the WHD-DOT device 2210 including, but not limited to: operating the WD-DOT device 2210 to obtain HD-DOT imaging data, performing DOT image reconstruction, obtaining a head model of the subject to be imaged, DOT signal noise reduction, and brain activity mapping.

FIG. 15 illustrates a computer system 2200 in one aspect. The computer system 2200 may include a computing device 2202, similar to the at least one computing devices illustrated in the block diagram of the WHD-DOT system of FIG. 1. In one aspect, the computing device 2202 is part of a server system 2204, which also includes a database server 2206. The computing device 2202 is in communication with a database 2208 through the database server 2206. The computing device 2202 is communicably coupled to the WHD-DOT device 2210, a head imaging device 2220, and a user computing device 2230 through a network 2250. The network 2250 may be any network that allows local area or wide area communication between the devices. For example, the network 2250 may allow communicative coupling to the Internet through at least one of many interfaces including, but not limited to, at least one of a network, such as the Internet, a local area network (LAN), a wide area network (WAN), an integrated services digital network (ISDN), a dial-up-connection, a digital subscriber line (DSL), a cellular phone connection, and a cable modem. The user computing device 2230 may be any device capable of accessing the Internet including, but not limited to, a desktop computer, a laptop computer, a personal digital assistant (PDA), a cellular phone, a smartphone, a tablet, a phablet, wearable electronics, smart watch, or other web-based connectable equipment or mobile devices.

In various aspects, the computing device 2202 is configured to operate the plurality of source and detector modules in a coordinated manner to acquire DOT signals from a plurality of detection channels using one or more of the signal encoding methods as described above. In some aspects, the computing device 2202 may be configured to perform essentially all operations associated with operating the plurality of source and detector modules of the WHD-DOT device 2210 including, but not limited to, producing a plurality of signals to activate each of the source modules, receiving raw detector signals from each ADC of each detector module, producing signals to frequency modulate the light produced by each source, frequency demodulating the raw signals received from the detector modules in response to frequency-modulated illumination, producing signals to modulate the gain of the TIA of each detector module, and any other operation associated with associated with operating the plurality of source and detector modules of the WHD-DOT device 2210 described herein without limitation. In other additional aspects, a portion of the operations associated with operating the plurality of source and detector modules of the WHD-DOT device 2210 may performed by the computing device 2202 and the remainder of the operations may be performed by the FPGA on the main board of the WHD-DOT device 2210 as described above (see FIG. 1).

a) Image Reconstruction

In other aspects, the computing device 2202 is configured to perform a plurality of tasks associated with reconstructing neuroimages based on the plurality of DOT signals acquired from a plurality of detection channels of the WHD-DOT device 2210. In various aspects, the computing device 2202 may perform neuroimage reconstruction using any known image reconstruction method including, but not limited to, back projection reconstruction methods.

In general, typical image reconstruction methods include registering a plurality of DOT measurements acquired from a plurality of detection channels to a volumetric model of the subject's brain. In one aspect, each DOT measurement of the plurality of DOT measurements is associated with one of the plurality of detection channels of the WHD-DOT device. In this aspect, the detection channel associated with each DOT measurement may obtained using at least one of the encoding schemes describe above. In addition, each detection channel may be registered to a position on a 3D map of the subject's brain.

b) Volumetric Head Model Construction

Without being limited to any particular theory, the accuracy of the algorithms for registering the plurality of DOT measurements of the DOT data set to a volumetric model of a specific subject's head anatomy are thought to influence the spatial resolution of HD-DOT functional localization. However, in young children and in a majority of patients with motor system disorders such as CP, the feasibility of obtaining research-quality MRIs suitable for producing high resolution volumetric head models may not be feasible. In the absence of MRIs of the subject's head, volumetric head models of the subject may be produced by transforming a reference (or atlas) anatomy to match the subject. In various aspects, the computing device 2202 may be configured and programmed to produce an individualized volumetric model of the subject's head using non-linear registration methods as described below. In one aspect, the non-linear registration method may include warping a previously stored atlas anatomy to the shape of a particular subject's head. In this aspect, localization errors associated with the non-linear registration method may be less than about 3 mm as determined by comparing positions of landmarks on a volumetric model produced using the atlas-based non-linear registration method to the positions of corresponding landmarks on an MRI-derived volumetric head models.

Figure 11C:
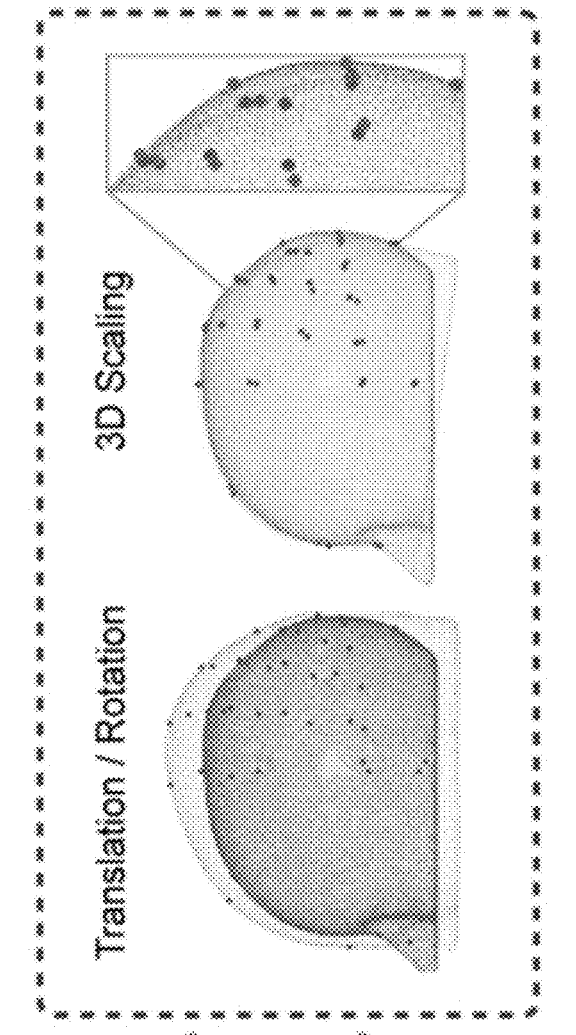
FIG. 11C is an image illustrating a method of obtaining a subject head model using registration by linear optimization.
Figure 11E:
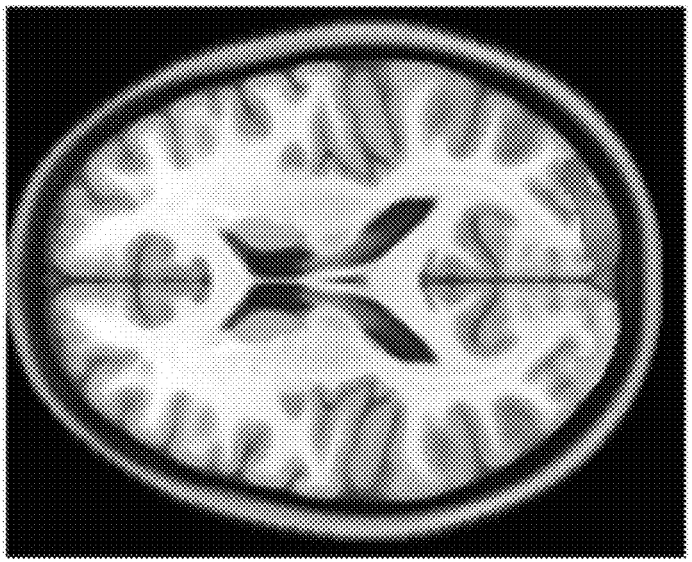
FIG. 11E is an image reconstructed from DOT data based on the subject-derived light model illustrated in FIGS. 11A-11D.
Figure 11D:
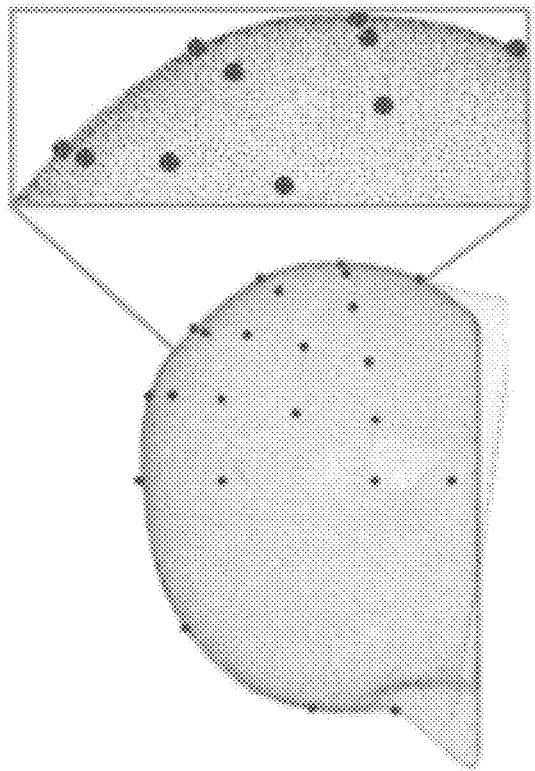
FIG. 11D is an image showing a subject head model obtained using additional registration by nonlinear optimization of the linearly-registered surface.
Figures 12A, 12B:
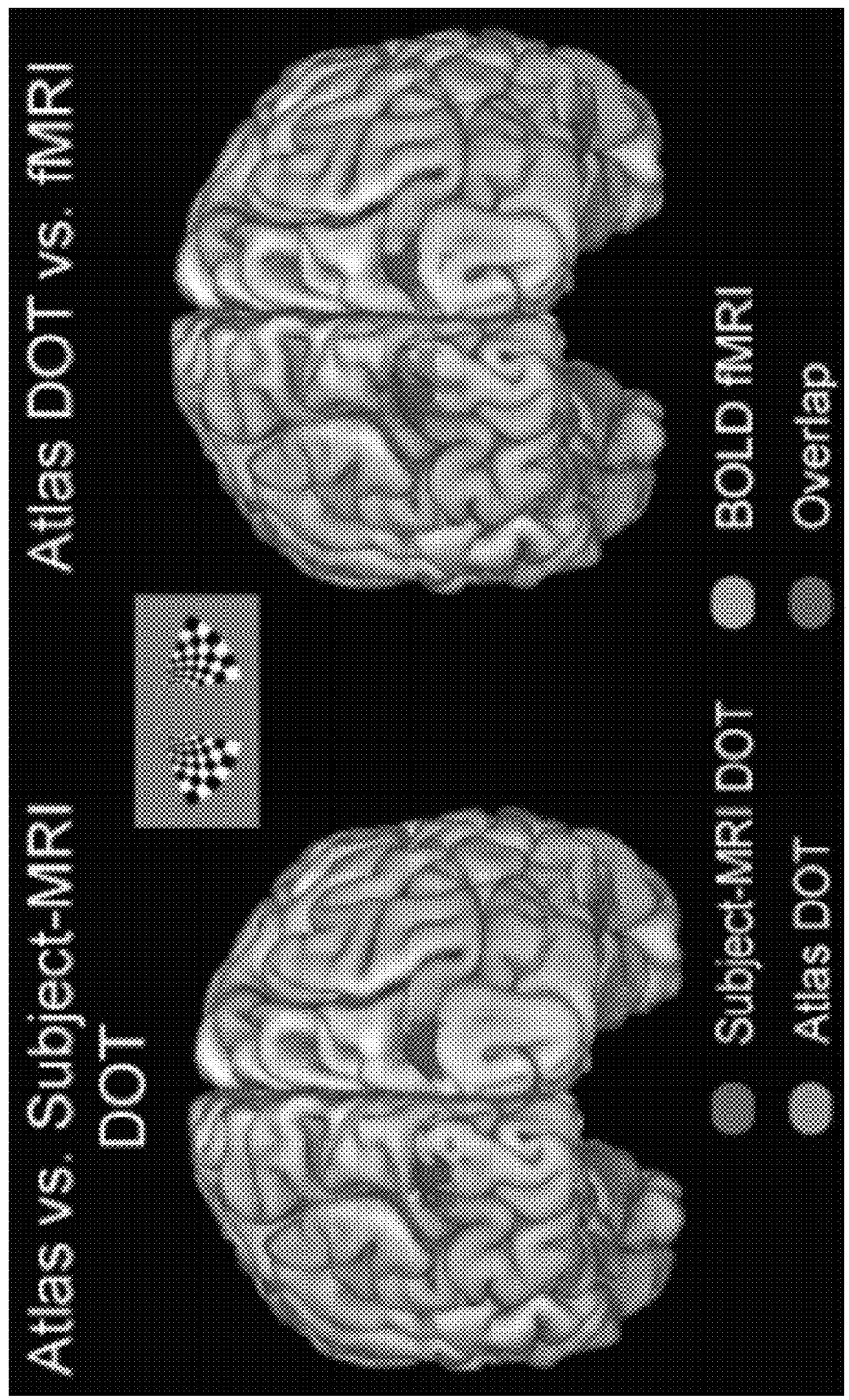
FIG. 12A is an image comparing neural activity maps reconstructed from DOT data using an atlas-derived head model and an MM-based head model.
FIG. 12B is an image comparing a neural activity map reconstructed from DOT data using an atlas-derived head model and neural activity map reconstructed from fMRI BOLD measurements.

In order to create anatomically accurate head models in the absence of a subject's MRI, reference anatomy models, based on population MM data, shown illustrated in FIG. 11A, may be used on one aspect. In this aspect, the computing device 2202 may be configured and programmed to warp each individual head surface, shown in FIG. 11B using two consecutive fitting routines: (1) a linear registration, for performing global adjustments as illustrated in FIG. 11C, and (2) a non-linear registration, for improving local fitting as illustrated in FIG. 11D. Additionally in this aspect, the computing device 2202 may be further configured and programmed to compute an individualized forward light model, illustrated in FIG. 13E, that is aligned with the subject's anatomical head structure, using the warped atlas and a co-registered array of source and detector arrays of the WHD-DOT device 2210 obtained as described below. This atlas-based head modeling approach has been validated in simulation using subject-specific anatomical images and subject-matched fMRI datasets, as illustrated in FIG. 12A and FIG. 12B. In various aspects, localization errors for atlas-derived vs subject-MM based head reconstruction models may be less than about 2 mm (see FIG. 12A) and localization errors for HD-DOT and fMRI may be less than about 6 mm (see FIG. 12B).

c) Head Surface Model Production

In various aspects, the computation of light-path models for individual subjects make use of an external head model representing the exterior shape of a subject's head as well as the relative location of the source and detector modules of the WHD-DOT device 2210. In various aspects, the computing device 2202 may be configured and programmed to efficiently capture photometric data and to produce a 3D model of the external surface of the subject's head and positions of the source and detector modules. As illustrated in FIG. 15, the WHD-DOT system 2200 may include a head imaging device 2220 communicably coupled to the computing device 2202 in one aspect. Any suitable head imaging device 2220 suitable for obtaining photometric data suitable for producing head surface models of an individual subject may be used including, but not limited to, a photometric scanner such as a Artec3D Spider scanner and a 3D motion capture device such as a Kinect system with KinectFusion Software.

In one aspect, the computing device 2202 may be configured and programmed to obtain the fiducial positions for data analysis photometry using the head imaging device 2220. In this aspect, a face tracking algorithm may enable 3D surface and texture capture while moving the sensor around the subject, as illustrated in FIG. 13A. In various aspects, anatomical landmarks based on the 10/20 international system may obtained using the head imaging device 2220 and used as fiducials, as illustrated in FIG. 13B and FIG. 13C. Non-limiting examples of anatomical landmarks based on the 10/20 international system include nasion, inion, pre-auricular points and Cz. In addition, the positions of selected source and detector modules of the imaging array of the WHD-DOT device 2210 may also be obtained using the head imaging device 2220, shown as blue dots in FIG. 13B and FIG. 13C. By way of non-limiting example, the Artec3D Spider may obtain 3D coordinates of sensor and detector modules and the subject's head surface in less than 5 minutes. In various aspects, photometry locational accuracy may be better than 1 mm.

In various aspects, the head and module surface measures obtained as described above are used in the reconstruction methods described above. In one aspect, an FEM head modeling algorithm may be used to model light propagation and inversion may proceed using known methods.

d) Noise Reduction of DOT Signals

In various aspects, the WHD-DOT system 2200 may further provide for de-noising the measured data to reduce motion artifacts in the reconstructed neuroimages. In some aspects, several existing methods including, but not limited to, ICA methods and wavelets methods, previously used in fMRI and fNIRS imaging, may be used for de-noising HD-DOT data sets. Without being limited to any particular theory, the overlapping ranges of detector channels, from which HD-DOT measurements are obtained, impose an inherent structure on potential movement-induced error signals. An algorithm, described below, may be applied to these overlapping measurements to quantify and remove source-detector coupling changes.

In various aspects, the computing device 2202 may be configured and programmed to reduce neuroimaging artifacts resulting from head motion of the subject using a novel coupling coefficient (CC) motion noise removal method. Without being limited to any particular theory, the coupling coefficient (CC) motion noise removal method leverages the covariance structure inherent to HD-DOT data due to the large number of overlapping measurements. In one aspect, the WHD-DOT system 220 may further include a head accelerometer 2212 Wireless tri-axial accelerometers (G-link-LXRS, MicroStrain) communicably coupled to the computing device 2202 and used to measure head motion.

In various aspects, the computing device 2202 may be configured and programmed to estimate coupling coefficients as either the mean of the nearest neighbors or as part of the inversion step. In these various aspects, the time-variant coupling coefficients may be modeled as: $I_{cor}$ [$C_{so}$/$C_s(t)$] *[$C_{do}$/$C_d(t)$] *I(t), where I(t) is a single SD-pair intensity, $I_{cor}(t)$ is corrected intensity, $C_s(t)$ is source coupling coefficient, $C_d(t)$ is detector coupling coefficient and $C_{so}$ and $C_{do}$ are the temporal mean of $C_s(t)$ and $C_d(t)$, respectively. For validation, the results may be compared to existing methods used previously in fMRI and fNIRS, including, but not limited to Independent Component Analysis (ICA), Wavelet Analysis, "Scrubbing" Data (cropping corrupted segments), and Polynomial spline interpolation.

Figure 16:
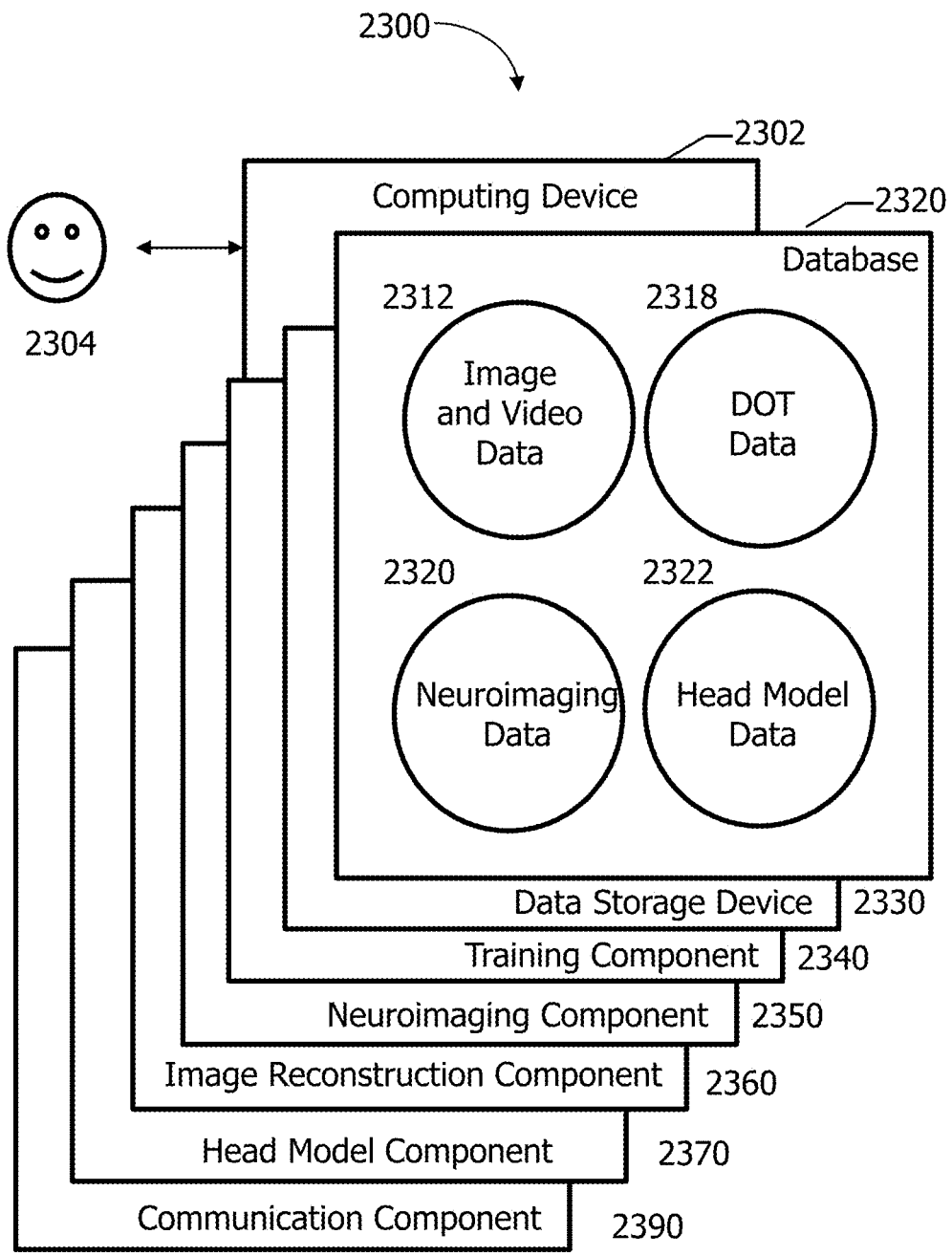
FIG. 16 is a block diagram schematically illustrating a WHD-DOT computing device in accordance with one aspect of the disclosure.

FIG. 16 depicts a component configuration 2300 of computing device 2302, which includes database 2320 along with other related computing components. In some aspects, computing device 2302 is similar to computing device 2202 (shown in FIG. 15). User 2304 may access components of computing device 802. In some aspects, database 810 is similar to database 2208 (shown in FIG. 15).

In the example aspect, database 2310 includes DOT data 2318, neuroimaging data 2320, and data defining a head model 820. Neuroimaging data 2330 may store neuroimaging data obtained by the WHD-DOT device.

Computing device 2302 also includes a number of components which perform specific tasks. In the example aspect, computing device 2302 includes data storage device 2330, neuroimaging component 2350, image reconstruction component 2360, therapy control component 2370, and communications component 2390. Data storage device 2330 is configured to store data received or generated by computing device 2302, such as any of the data stored in database 2310 or any outputs of processes implemented by any component of computing device 2302. Neuroimaging component 2350 is configured to perform at least a portion of the tasks associated with neuroimaging using the WHD-DOT device as described above. In a further aspect, head model component 2370 produces volumetric head models, head surface models, and light path models using the methods described above. Image reconstruction component 2360 produces neuroimages from the plurality of DOT signals acquired by the WHD-DOT device using the methods described above. Communication component 2390 is configured to enable communications between computing device 2302 and other devices (e.g. user computing device 2230, WHD-DOT device 2210, head accelerometer 2212, and head imaging device 2220, all shown in FIG. 15) over a network, such as network 2250 (shown in FIG. 15), or a plurality of network connections using predefined network protocols such as TCP/IP (Transmission Control Protocol/Internet Protocol).

Figure 17:
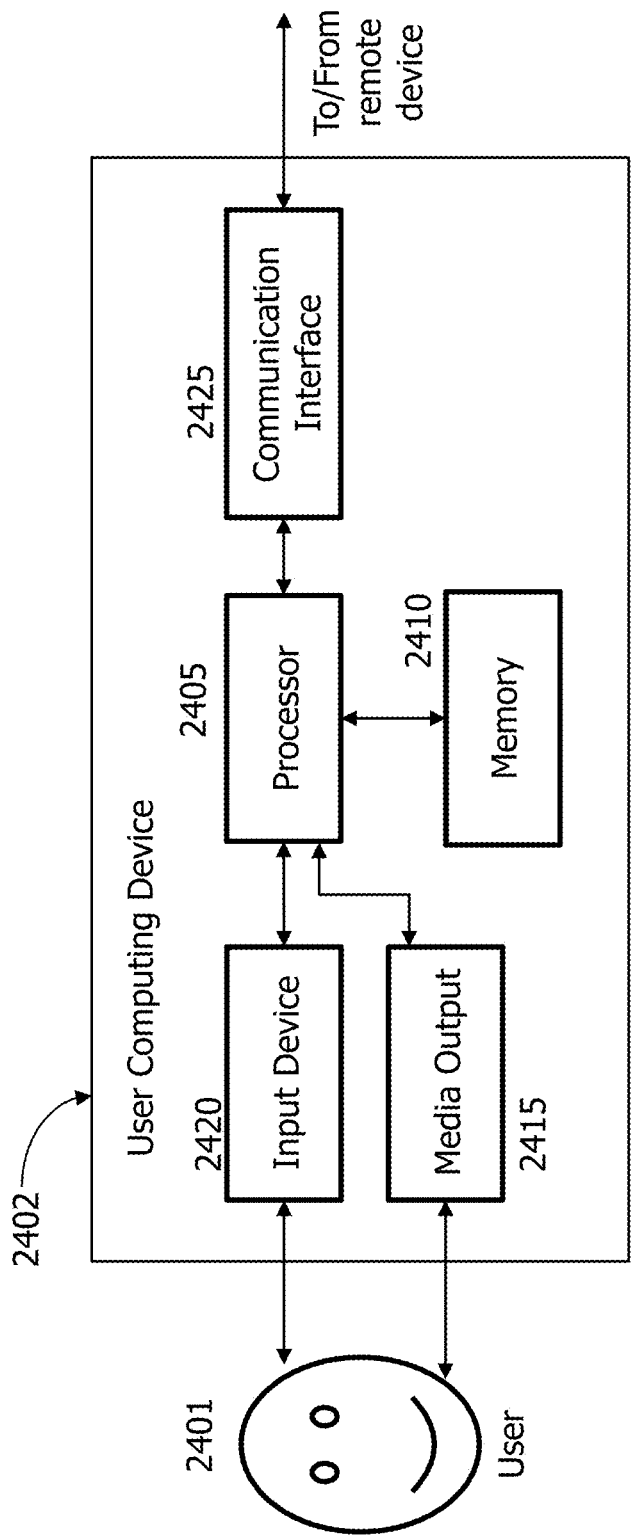
FIG. 17 is a block diagram schematically illustrating a remote or user computing device in accordance with one aspect of the disclosure.

FIG. 17 depicts a configuration of a remote or user computing device 2402, such as user computing device 2230 (shown in FIG. 15). Computing device 2402 may include a processor 2405 for executing instructions. In some aspects, executable instructions may be stored in a memory area 2410. Processor 2405 may include one or more processing units (e.g., in a multi-core configuration). Memory area 2410 may be any device allowing information such as executable instructions and/or other data to be stored and retrieved. Memory area 2410 may include one or more computer-readable media.

Computing device 2402 may also include at least one media output component 2415 for presenting information to a user 2401. Media output component 2415 may be any component capable of conveying information to user 2401. In some aspects, media output component 2415 may include an output adapter, such as a video adapter and/or an audio adapter. An output adapter may be operatively coupled to processor 2405 and operatively coupleable to an output device such as a display device (e.g., a liquid crystal display (LCD), organic light emitting diode (OLED) display, cathode ray tube (CRT), or "electronic ink" display) or an audio output device (e.g., a speaker or headphones). In some aspects, media output component 2415 may be configured to present an interactive user interface (e.g., a web browser or client application) to user 2401.

In some aspects, computing device 2402 may include an input device 2420 for receiving input from user 2401. Input device 2420 may include, for example, a keyboard, a pointing device, a mouse, a stylus, a touch sensitive panel (e.g., a touch pad or a touch screen), a camera, a gyroscope, an accelerometer, a position detector, and/or an audio input device. A single component such as a touch screen may function as both an output device of media output component 2415 and input device 2420.

Computing device 2402 may also include a communication interface 2425, which may be communicatively coupleable to a remote device. Communication interface 2425 may include, for example, a wired or wireless network adapter or a wireless data transceiver for use with a mobile phone network (e.g., Global System for Mobile communications (GSM), 3G, 4G or Bluetooth) or other mobile data network (e.g., Worldwide Interoperability for Microwave Access (WIMAX)).

Stored in memory area 2410 are, for example, computer-readable instructions for providing a user interface to user 2401 via media output component 2415 and, optionally, receiving and processing input from input device 2420. A user interface may include, among other possibilities, a web browser and client application. Web browsers enable users 2401 to display and interact with media and other information typically embedded on a web page or a website from a web server. A client application allows users 2401 to interact with a server application associated with, for example, a vendor or business.

Figure 18:
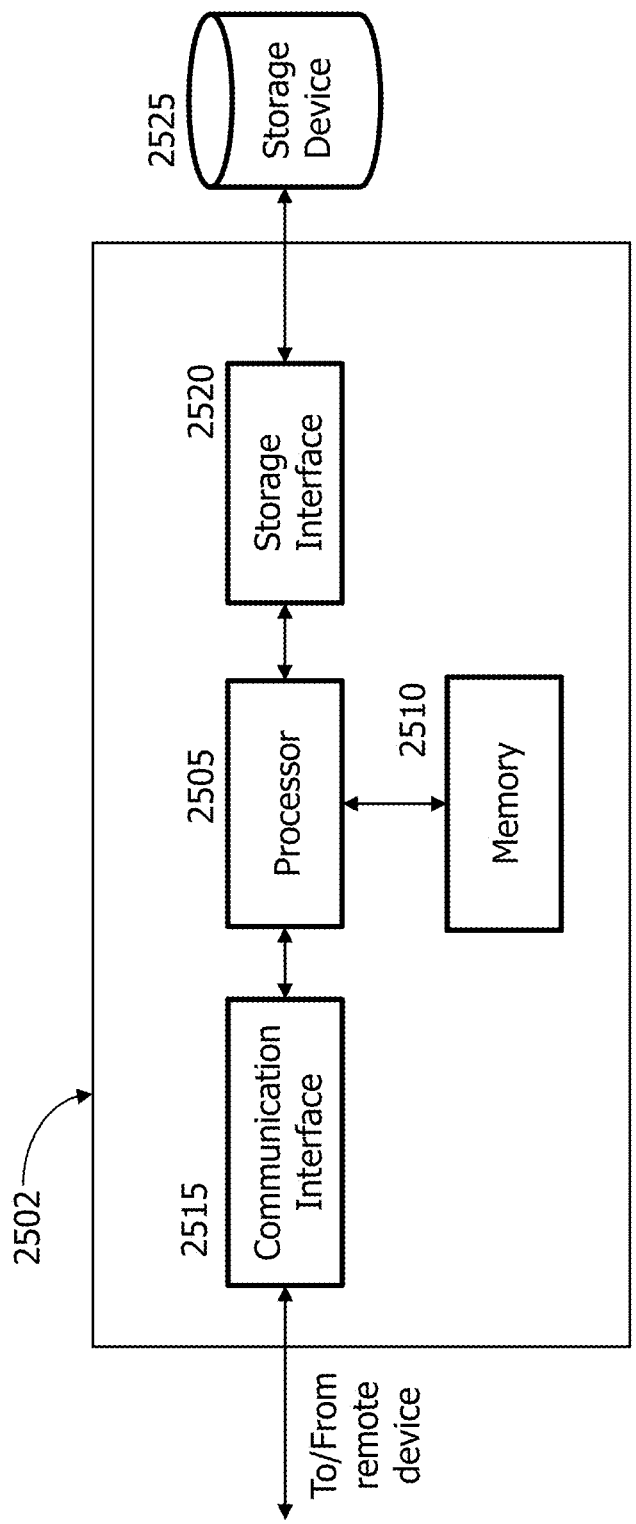
FIG. 18 is a schematically illustrating a server system in accordance with one aspect of the disclosure.

FIG. 18 illustrates an example configuration of a server system 2502. Server system 2502 may include, but is not limited to, database server 2206 and computing device 2202 (both shown in FIG. 15). In some aspects, server system 2502 is similar to server system 2204 (shown in FIG. 15). Server system 2502 may include a processor 2505 for executing instructions. Instructions may be stored in a memory area 2525, for example. Processor 2505 may include one or more processing units (e.g., in a multi-core configuration).

Processor 2505 may be operatively coupled to a communication interface 2515 such that server system 2502 may be capable of communicating with a remote device such as user computing device 2230 (shown in FIG. 15) or another server system 2502. For example, communication interface 2515 may receive requests from user computing device 2230 via a network 2250 (shown in FIG. 15).

Processor 2505 may also be operatively coupled to a storage device 2525. Storage device 2525 may be any computer-operated hardware suitable for storing and/or retrieving data. In some aspects, storage device 2525 may be integrated in server system 2502. For example, server system 2502 may include one or more hard disk drives as storage device 2525. In other aspects, storage device 2525 may be external to server system 2502 and may be accessed by a plurality of server systems 2502. For example, storage device 2525 may include multiple storage units such as hard disks or solid state disks in a redundant array of inexpensive disks (RAID) configuration. Storage device 2525 may include a storage area network (SAN) and/or a network attached storage (NAS) system.

In some aspects, processor 2505 may be operatively coupled to storage device 2525 via a storage interface 2520. Storage interface 2520 may be any component capable of providing processor 2505 with access to storage device 2525. Storage interface 2520 may include, for example, an Advanced Technology Attachment (ATA) adapter, a Serial ATA (SATA) adapter, a Small Computer System Interface (SCSI) adapter, a RAID controller, a SAN adapter, a network adapter, and/or any component providing processor 2505 with access to storage device 2525.

Memory areas 2410 (shown in FIG. 17) and 2510 may include, but are not limited to, random access memory (RAM) such as dynamic RAM (DRAM) or static RAM (SRAM), read-only memory (ROM), erasable programmable read-only memory (EPROM), electrically erasable programmable read-only memory (EEPROM), and non-volatile RAM (NVRAM). The above memory types are example only, and are thus not limiting as to the types of memory usable for storage of a computer program.

The computer systems and computer-implemented methods discussed herein may include additional, less, or alternate actions and/or functionalities, including those discussed elsewhere herein. The computer systems may include or be implemented via computer-executable instructions stored on non-transitory computer-readable media. The methods may be implemented via one or more local or remote processors, transceivers, servers, and/or sensors (such as processors, transceivers, servers, and/or sensors mounted on vehicle or mobile devices, or associated with smart infrastructure or remote servers), and/or via computer executable instructions stored on non-transitory computer-readable media or medium.

In some aspects, a computing device is configured to implement machine learning, such that the computing device "learns" to analyze, organize, and/or process data without being explicitly programmed. Machine learning may be implemented through machine learning (ML) methods and algorithms. In one aspect, a machine learning (ML) module is configured to implement ML methods and algorithms. In some aspects, ML methods and algorithms are applied to data inputs and generate machine learning (ML) outputs. Data inputs may include but are not limited to: images or frames of a video, object characteristics, and object categorizations. Data inputs may further include: sensor data, image data, video data, telematics data, authentication data, authorization data, security data, mobile device data, geolocation information, transaction data, personal identification data, financial data, usage data, weather pattern data, "big data" sets, and/or user preference data. ML outputs may include but are not limited to: a tracked shape output, categorization of an object, categorization of a type of motion, a diagnosis based on motion of an object, motion analysis of an object, and trained model parameters ML outputs may further include: speech recognition, image or video recognition, medical diagnoses, statistical or financial models, autonomous vehicle decision-making models, robotics behavior modeling, fraud detection analysis, user recommendations and personalization, game AI, skill acquisition, targeted marketing, big data visualization, weather forecasting, and/or information extracted about a computer device, a user, a home, a vehicle, or a party of a transaction. In some aspects, data inputs may include certain ML outputs.

In some aspects, at least one of a plurality of ML methods and algorithms may be applied, which may include but are not limited to: linear or logistic regression, instance-based algorithms, regularization algorithms, decision trees, Bayesian networks, cluster analysis, association rule learning, artificial neural networks, deep learning, dimensionality reduction, and support vector machines. In various aspects, the implemented ML methods and algorithms are directed toward at least one of a plurality of categorizations of machine learning, such as supervised learning, unsupervised learning, and reinforcement learning.

In one aspect, ML methods and algorithms are directed toward supervised learning, which involves identifying patterns in existing data to make predictions about subsequently received data. Specifically, ML methods and algorithms directed toward supervised learning are "trained" through training data, which includes example inputs and associated example outputs. Based on the training data, the ML methods and algorithms may generate a predictive function which maps outputs to inputs and utilize the predictive function to generate ML outputs based on data inputs. The example inputs and example outputs of the training data may include any of the data inputs or ML outputs described above. For example, a ML module may receive training data comprising customer identification and geographic information and an associated customer category, generate a model which maps customer categories to customer identification and geographic information, and generate a ML output comprising a customer category for subsequently received data inputs including customer identification and geographic information.

In another aspect, ML methods and algorithms are directed toward unsupervised learning, which involves finding meaningful relationships in unorganized data. Unlike supervised learning, unsupervised learning does not involve user-initiated training based on example inputs with associated outputs. Rather, in unsupervised learning, unlabeled data, which may be any combination of data inputs and/or ML outputs as described above, is organized according to an algorithm-determined relationship. In one aspect, a ML module receives unlabeled data comprising customer purchase information, customer mobile device information, and customer geolocation information, and the ML module employs an unsupervised learning method such as "clustering" to identify patterns and organize the unlabeled data into meaningful groups. The newly organized data may be used, for example, to extract further information about a customer's spending habits.

In yet another aspect, ML methods and algorithms are directed toward reinforcement learning, which involves optimizing outputs based on feedback from a reward signal. Specifically ML methods and algorithms directed toward reinforcement learning may receive a user-defined reward signal definition, receive a data input, utilize a decision-making model to generate a ML output based on the data input, receive a reward signal based on the reward signal definition and the ML output, and alter the decision-making model so as to receive a stronger reward signal for subsequently generated ML outputs. The reward signal definition may be based on any of the data inputs or ML outputs described above. In one aspect, a ML module implements reinforcement learning in a user recommendation application. The ML module may utilize a decision-making model to generate a ranked list of options based on user information received from the user and may further receive selection data based on a user selection of one of the ranked options. A reward signal may be generated based on comparing the selection data to the ranking of the selected option. The ML module may update the decision-making model such that subsequently generated rankings more accurately predict a user selection.

As will be appreciated based upon the foregoing specification, the above-described aspects of the disclosure may be implemented using computer programming or engineering techniques including computer software, firmware, hardware or any combination or subset thereof. Any such resulting program, having computer-readable code means, may be embodied or provided within one or more computer-readable media, thereby making a computer program product, i.e., an article of manufacture, according to the discussed aspects of the disclosure. The computer-readable media may be, for example, but is not limited to, a fixed (hard) drive, diskette, optical disk, magnetic tape, semiconductor memory such as read-only memory (ROM), and/or any transmitting/receiving medium, such as the Internet or other communication network or link. The article of manufacture containing the computer code may be made and/or used by executing the code directly from one medium, by copying the code from one medium to another medium, or by transmitting the code over a network.

These computer programs (also known as programs, software, software applications, "apps", or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The "machine-readable medium" and "computer-readable medium," however, do not include transitory signals. The term "machine-readable signal" refers to any signal used to provide machine instructions and/or data to a programmable processor.

As used herein, a processor may include any programmable system including systems using micro-controllers, reduced instruction set circuits (RISC), application specific integrated circuits (ASICs), logic circuits, and any other circuit or processor capable of executing the functions described herein. The above examples are example only, and are thus not intended to limit in any way the definition and/or meaning of the term "processor."

As used herein, the terms "software" and "firmware" are interchangeable, and include any computer program stored in memory for execution by a processor, including RAM memory, ROM memory, EPROM memory, EEPROM memory, and non-volatile RAM (NVRAM) memory. The above memory types are example only, and are thus not limiting as to the types of memory usable for storage of a computer program.

In one aspect, a computer program is provided, and the program is embodied on a computer readable medium. In one aspect, the system is executed on a single computer system, without requiring a connection to a sever computer. In a further aspect, the system is being run in a Windows® environment (Windows is a registered trademark of Microsoft Corporation, Redmond, Wash.). In yet another aspect, the system is run on a mainframe environment and a UNIX® server environment (UNIX is a registered trademark of X/Open Company Limited located in Reading, Berkshire, United Kingdom). The application is flexible and designed to run in various different environments without compromising any major functionality.

In some aspects, the system includes multiple components distributed among a plurality of computing devices. One or more components may be in the form of computer-executable instructions embodied in a computer-readable medium. The systems and processes are not limited to the specific aspects described herein. In addition, components of each system and each process can be practiced independent and separate from other components and processes described herein. Each component and process can also be used in combination with other assembly packages and processes. The present aspects may enhance the functionality and functioning of computers and/or computer systems.

EXAMPLES

Example 1: WHD-DOT System Performance

Figure 8B:
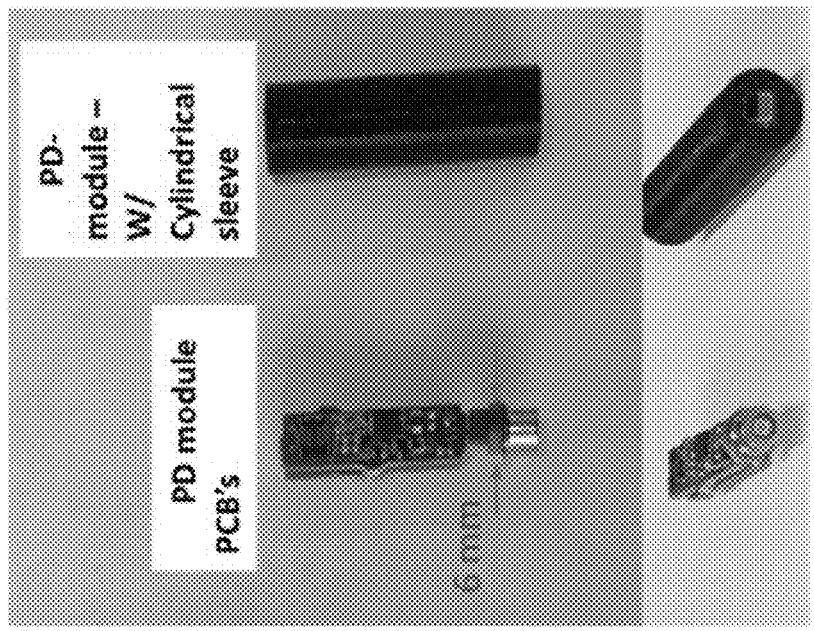
FIG. 8B contains an images of a small form factor wearable detection module in accordance with one aspect of the disclosure.
Figure 8A:
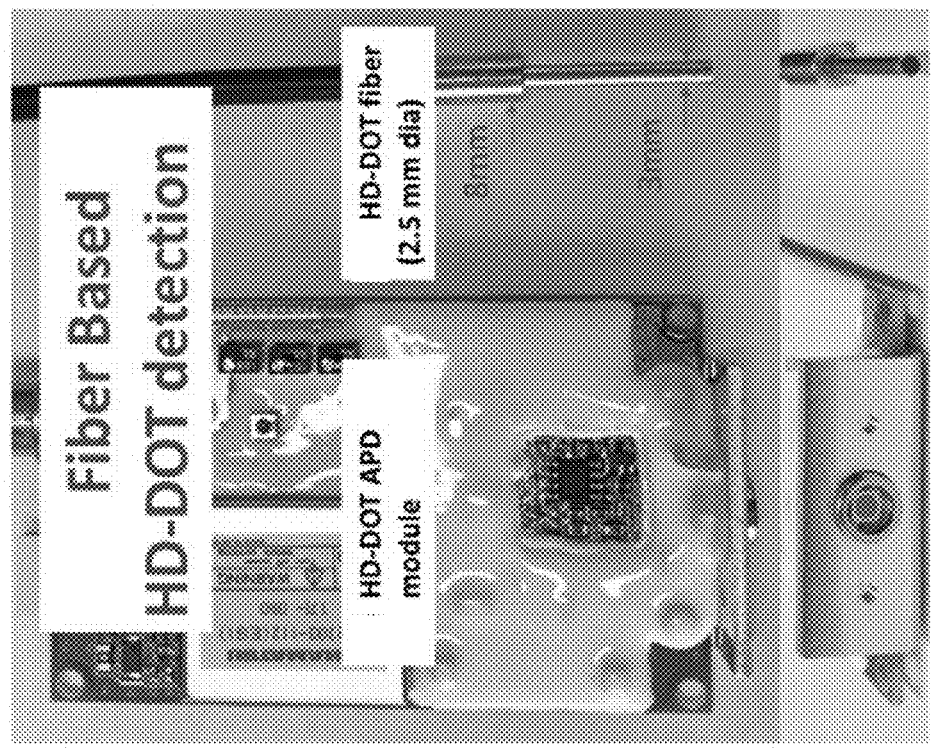
FIG. 8A contains an image of detectors from an existing fiber-based HD-DOT system.
Figure 9:
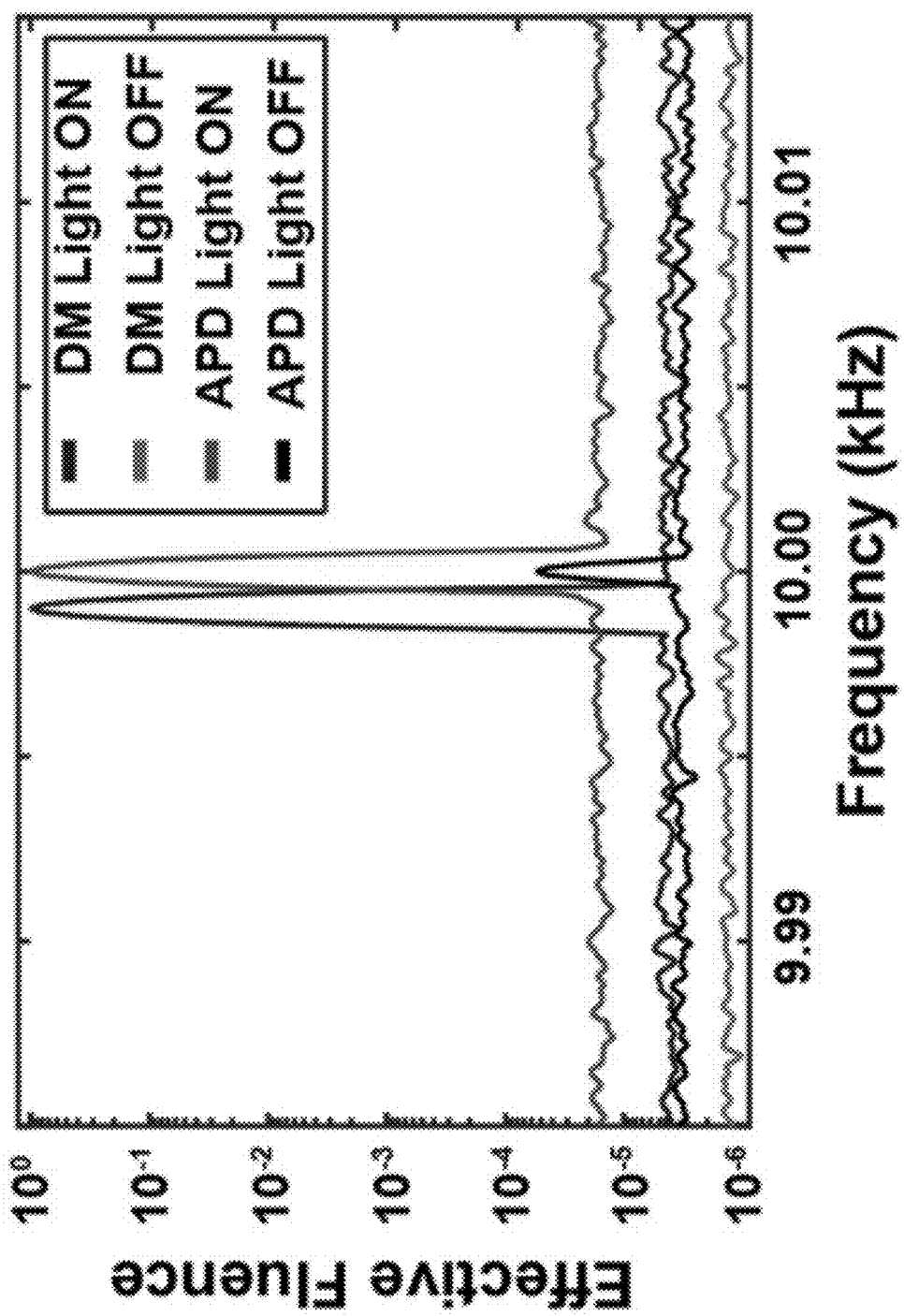
FIG. 9 is a graph comparing measured effective fluence as a function of light frequency obtained using an analog PD (APD) and a detection module (DM) in accordance with one aspect of the disclosure.
Figure 10:
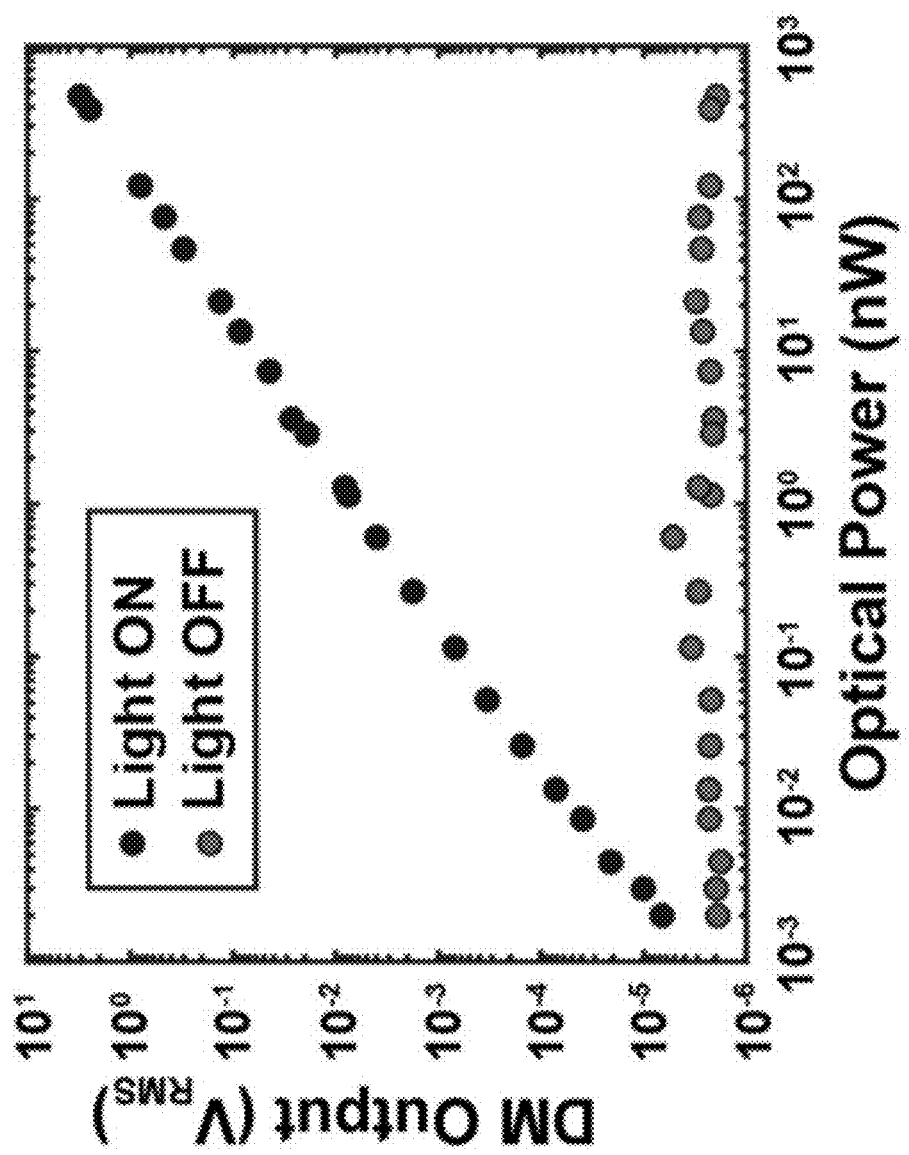
FIG. 10 is a graph of output signal of a detection module in accordance with one aspect of the disclosure as a function of optical power.

To validate the performance of the WHD-DOT system, the following experiments were conducted:

The operability of the small form factor detector module was demonstrated for the detection module (DM) of the disclosed WHD-DOT system, as illustrated in FIG. 9 and FIG. 10. The challenge was to reproduce the performance of the APD module (FIG. 9) in a space that approached the size of the fibers used for HD-DOT (see FIG. 8A and FIG. 8B). In one aspect, the PDM included a photodiode (PD), a transimpedance amplifier (TIA), and an analog-to-digital-converter (ADC) circuit. A prototype was developed through several design iterations, beginning with a large protoboard and extending down to the current small form factor PDM that was 6 mm in width and fit inside of a cylinder with 20 mm in length, as shown in the images of FIG. 8B. The design flow used Eagle (Autodesk) for circuit design and board layout/printed circuit board (PCB) design. The PCBs were fabricated using photo-lithography process based on artwork or a PCB design exported to EIA RS274x (Gerber) standard files and uploaded to Sunstone Circuit and assembled into a board by Screaming Circuits using a robotic soldering machine to assemble the PDM circuit for the WHD-DOT detection module.

Figure 3:
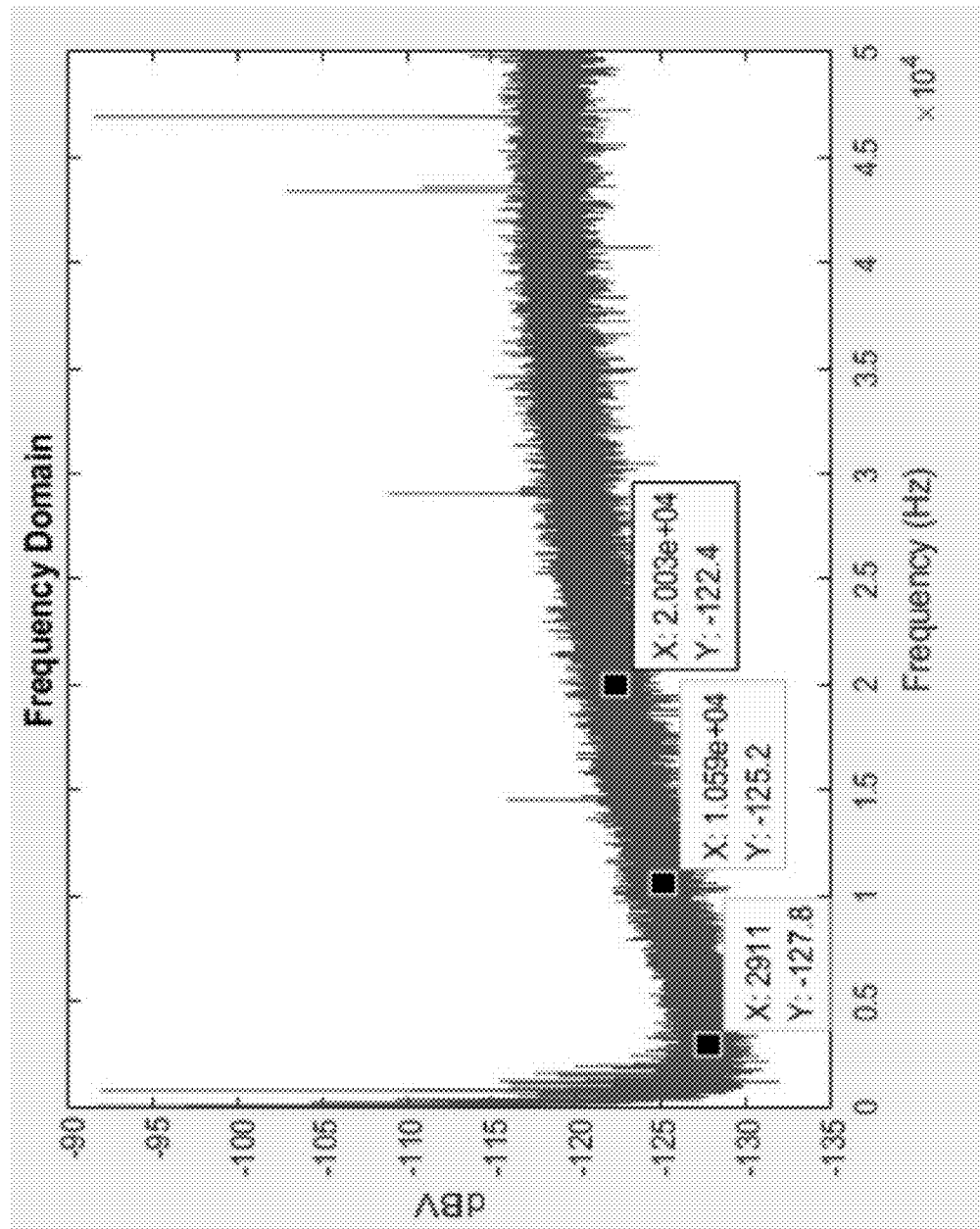
FIG. 3 is a graph summarizing the noise spectrum for a dark detector while a neighboring detector is stimulated with a full scale optical input at 10 KHz.

Through several designs iterations, a prototype PD/TIA/ADC of the detector module that provided detectivity, DNR and CT that rivaled C12703-01 APD specs, was developed. By way of non-limiting example, a 1 source/2 detector system was developed. The detectors were each powered off separate bench power supplies and enclosed in a 1 U rack with the performance shown below. The 750 nm source (see FIG. 3) was pulsed at 10 kHz and was connected to one of the detectors with a fiber optic cable. The other detector had a cap over its photodiode. The same optical power, modulated at 10 kHz, was input to both the PDM and a reference APD. The PDM had a lower detectivity threshold than the reference APD for the effective fluence received on a head (power/collection area) (FIG. 9). The experiment demonstrated that the PDM matches dynamic range of the reference APD module dynamic range and has lower crosstalk (FIG. 10). The full results of the experiment are as follows: NEP: 97 fW/sqrt(Hz) at 20 KHz, 69 fW/sqrt(Hz) at 10 KHz; Sensitivity: 8.1 M; Dynamic Range: 144 dB; Detectivity: 61.4 fW/sqrt(Hz) at 10 KHz; and Crosstalk: 113 dB.

In various aspects, tests with the full implementation of a WHD-DOT system were used to confirm the anticipated system specifications. In vivo tests provided realistic cranial tissue structures and subject movement. Functional imaging in healthy adults (N=20) for visual, auditory, and language tasks and rest followed known protocols (FIG. 7).

This written description uses examples to disclose the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A fiber-less detector module for a high-density diffuse optical tomography instrument, the fiber-less detector module comprising:
a photodiode;
a transimpedance amplifier operatively coupled to the photodiode;
an analog to digital converter operatively coupled to the transimpedance amplifier;
and a housing having a tip end and containing the photodiode, the transimpedance amplifier, the analog to digital converter, and a wire interface for outputting a digital signal from the analog to digital converter to a control module, wherein the detector module is configured to be mounted on a wearable device with the tip end of the housing extending through the wearable device to allow the detector module to contact a scalp of a subject and to receive light from the scalp of the subject at a detector position.

2. The fiber-less detector module of claim 1, wherein the housing comprises a maximum width ranging from about 1 mm to about 6 mm and a length ranging from about 10 mm to about 30 mm.

3. The fiber-less detector module of claim 2, wherein the photodiode comprises a sensor area ranging from about 1 $mm^2$ to about 6 $mm^2$.

4. The fiber-less detector module of claim 3, further comprising a detectivity of less than about 300 fW/sqrt (Hz).

5. The fiber-less detector module of claim 1, wherein the housing further comprises a pair of fiducial markings, the fiducial markings configured to uniquely identify at least one of: the detector position and an orientation of the housing relative to the scalp of the subject.

6. The fiber-less detector module of claim 1, further comprising a light pipe optically coupled to the photodiode, the light pipe configurable to transmit light from the scalp of the subject at the detector position to the photodiode.

7. A wearable device for high-density-diffuse optical tomography, the wearable device comprising:
a plurality of source modules, each source module comprising a source housing containing a light source, each source housing configurable to contact a scalp of a subject and to deliver light into the scalp at one source position of a plurality of source positions;
a plurality of detector modules, each detector module comprising a detector housing containing a photodiode, a transimpedance amplifier operatively coupled to the photodiode, and an analog to digital converter operatively coupled to the transimpedance amplifier, the detector housing containing at least one of the photodiode, wherein each detector housing is mounted on the wearable device to allow the detector module to contact the scalp of the subject and is configurable to receive light from the scalp at one detector position of a plurality of detector positions;
a flexible cap configured to fit over the scalp of the subject, the plurality of source modules and the plurality of detector modules coupled to and extending at least partially through the flexible cap to form a plurality of brush tips to contact the scalp of the subject when the subject is wearing the flexible cap; and
a control circuit operatively coupled to the plurality of source modules and to the plurality of detector modules, the control circuit configured to operate the plurality of source modules and the plurality of detector modules in a coordinated manner to acquire a plurality of diffuse optical tomography measurements.

8. The wearable device of claim 7, wherein the control circuit comprises a control module selected from the group consisting of a microcontroller, a central processing unit, and a field programmable gate array, the control module operatively connected to a plurality of source drivers and to the plurality of detector modules, each source driver operatively connected to one light source of one source module.

9. The wearable device of claim 8, wherein the control circuit further comprises a data interface operatively connected to the control module, the data interface operatively coupled to a computing device comprising a processor, wherein the data interface is selected from the group consisting of a USB3 interface and a wireless transceiver interface.

10. The wearable device of claim 9, wherein the processor is configured to transform the plurality of diffuse optical tomography measurements to a map of brain activation of the subject according to a model, the model selected from the group consisting of a homogeneous model, a layered model, a sphere model, a hemisphere model, a cylindrically-shaped model, and an anatomically derived model with finite element analysis.

11. The wearable device of claim 9, wherein the control circuit further comprises a plurality of quadrature modulators and a plurality of quadrature demodulators, each quadrature modulator operatively connected between the control module and one source driver of the plurality of source drivers, and each quadrature demodulator operatively connected between the control module and one detector module of the plurality of detector modules.

12. The wearable device of claim 7, wherein the flexible cap comprises a plurality of embedded module fittings configured to operatively couple the plurality of source modules and the plurality of detector modules with the plurality of detector modules extending at least partially through the flexible cap and to maintain the plurality of source modules and the plurality of detector modules in an array pattern, wherein the array pattern comprises a plurality of source-detector channels, each source-detector channel comprising one source module and one detector module separated by a nearest-neighbor distance, wherein light produced by the one source module is detectable by the one detector module at the nearest-neighbor distance.

13. The wearable device of claim 12, wherein the nearest-neighbor distance is selected from the group consisting of a first nearest-neighbor distance ranging from about 0.5 cm to about 1.3 cm, a second nearest neighbor distance ranging from about 1.0 to about 3.0 cm, and a third nearest neighbor distance ranging from about 1.0 and about 5.0 cm.

14. The wearable device of claim 13, wherein the source housing and the detector housing each comprise a maximum width ranging from about 1 mm to about 6 mm and a length ranging from about 10 mm to about 30 mm.

15. The wearable device of claim 14, wherein the photodiode comprises a sensor area ranging from about 1 $mm^2$ to about 6 $mm^2$.

16. The wearable device of claim 15, wherein the wearable device is characterized by an NEP of less than about 300 fW/sqrt(Hz), a detectivity of less than about 50 NEP/mm2, a dynamic range of less than about 80 dB, and a cross talk of less than about −80 dB.

17. The wearable device of claim 16, wherein each source housing and each detector housing further comprise a pair of fiducial markings, the fiducial markings configured to uniquely identify at least one of a position and an orientation of each source housing and each detector relative to the scalp of the subject.

18. The wearable device of claim 16, wherein each source module and each detector module further comprise a light pipe, the light pipe optically coupled to the light source of each source module or optically coupled to the detector of each detector module, the light pipe configurable to transmit light from the light source into the scalp at the source position or to transmit light from the scalp at the detector position into the photodiode.

19. A method for obtaining a series of brain activity maps of a subject using a wearable high-diffuse optical tomography (WHD-DOT) device, the method comprising:
   a) fitting the WHD-DOT device to a scalp of the subject, wherein the WHD-DOT device comprises a flexible cap, a plurality of source modules and detector modules coupled to the flexible cap in an array pattern, a plurality of brush tips, each brush tip containing one of the plurality of source modules or one of the plurality of detector modules, wherein each brush tip allows its source module or detector module to contact the scalp of the subject, and a control circuit comprising at least one control module selected from the group consisting of a microcontroller, a central processing unit, and a field programmable gate array, the at least one control module operatively coupled to the plurality of source modules and detector modules, the at least one control module configured to operate the plurality of source modules and detector modules according to at least one encoding scheme, wherein each source module and detector module comprises a housing with a maximum width ranging from about 1 mm to about 6 mm and a length ranging from about 10 mm to about 30 mm; and
   b) operating, under control of the at least one control module, the plurality of source modules and detector modules to obtain a plurality of diffuse optical tomography measurements, each diffuse optical tomography measurement associated with a source-detector channel of the WHD-DOT device.

20. The method of claim 19, further comprising:
   c) transforming, using a processor of a computing device operatively coupled to the at least one control module, the plurality of diffuse optical tomography measurements to a map of brain activation of the subject according to a model, the model selected from the group consisting of a homogeneous model, a layered model, a sphere model, a hemisphere model, a cylindrically-shaped model, and an anatomically derived model with finite element analysis.

* * * * *

UNITED STATES PATENT AND TRADEMARK OFFICE
CERTIFICATE OF CORRECTION

PATENT NO. : 11,864,865 B2
APPLICATION NO. : 16/286194
DATED : January 9, 2024
INVENTOR(S) : Joseph Culver et al.

It is certified that error appears in the above-identified patent and that said Letters Patent is hereby corrected as shown below:

In the Specification

In Column 1, Lines 17-19 should read:
-- This invention was made with government support under grant R01NS090874 and EB027005, awarded by the National Institutes of Health. The government has certain rights in the invention. --.

Signed and Sealed this
Nineteenth Day of November, 2024

Katherine Kelly Vidal
*Director of the United States Patent and Trademark Office*